(12) United States Patent
Silverman et al.

(10) Patent No.: US 8,735,606 B2
(45) Date of Patent: May 27, 2014

(54) THIOPHENE-2-CARBOXIMIDAMIDE BASED SELECTIVE NEURONAL NITRIC OXIDE INHIBITORS

(71) Applicant: Northwestern University, Evanston, IL (US)

(72) Inventors: Richard B. Silverman, Winnetka, IL (US); He Huang, Chicago, IL (US); Qing Jing, Morton Grove, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/015,551

(22) Filed: Aug. 30, 2013

(65) Prior Publication Data

US 2014/0066635 A1    Mar. 6, 2014

Related U.S. Application Data

(60) Provisional application No. 61/774,926, filed on Mar. 8, 2013, provisional application No. 61/698,249, filed on Sep. 7, 2012, provisional application No. 61/695,187, filed on Aug. 30, 2012.

(51) Int. Cl.
*C07D 409/12* (2006.01)

(52) U.S. Cl.
USPC .......................................................... 549/59

(58) Field of Classification Search
USPC ........................................................... 549/59
See application file for complete search history.

(56) References Cited

U.S. PATENT DOCUMENTS 6,809,088 B2 * 10/2004 Chabrier de Lassauniere et al. ............................ 514/183

* cited by examiner

*Primary Examiner* — Kristin Vajda
(74) *Attorney, Agent, or Firm* — Reinhart Boerner Van Deuren s.c.

(57) ABSTRACT

Selective neuronal nitric oxide synthase (nNOS) inhibitor compounds designed with one or more thiophene-2-carboximidamide substituents for improved bioavailability.

1 Claim, 6 Drawing Sheets

R = F, X= O
R = F, X = NH
R = Cl, X=O
R = Cl, X=NH
R = Br, X =O
R = Br, X =NH

THIOPHENE-2-CARBOXIMIDAMIDE BASED SELECTIVE NEURONAL NITRIC OXIDE INHIBITORS

This application claims priority benefit from application Ser. No. 61/695,187 filed Aug. 30, 2012, application Ser. No. 61/698,249 filed Sep. 7, 2012 and application Ser. No. 61/774,926 filed Mar. 8, 2013—each of which is incorporated herein by reference in its entirety.

This invention was made with government support under grant number GM049725 awarded by the National Institutes of Health. The government has certain rights in the invention.

BACKGROUND OF THE INVENTION

Neuronal nitric oxide synthase (nNOS) catalyzes the oxidation of L-arginine to L-citrulline in the central nervous system, generating nitric oxide (NO), a critical neurotransmitter. Significant research has implicated the overexpression of nNOS—and overproduction of NO—in various neurological diseases, including Parkinson's, Alzheimer's, and Huntington's diseases, as well as neuronal damage due to stroke, cerebral palsy and migraine headaches. Inhibiting endothelial nitric oxide synthase (eNOS) and inducible nitric oxide synthase (iNOS) is, however, undesirable, because these isozymes are responsible for maintaining crucial body function. Thus, selective inhibition of nNOS over its closely related isoforms, eNOS and iNOS, has provided a promising strategy in the development of therapeutics for the treatment of neurodegenerative diseases. However, while certain compounds have exhibited good potency and high selectivity, they often suffer from poor bioavailability. As a result, there remains an on-going search in the art for effective bioavailable NOS inhibitors to realize the therapeutic potential of such compounds.

SUMMARY OF THE INVENTION

In light of the foregoing, it is an object of the present invention to provide compounds, compositions and related methods of use for the selective inhibition of neuronal nitric oxide synthase, thereby overcoming various deficiencies and shortcomings of the prior art including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more small molecule non-peptide compounds exhibiting selective nNOS inhibition over other enzyme isoforms and providing improved bioavailability—including compounds that are orally active.

It can be another object of the present invention to provide one or more such compounds for in vitro use and study under conditions promoting nitric oxide production, indicative of one or more mammalian disease states.

Alternatively, it can also be an object of the present invention to provide one or more such compounds enabling in vivo treatment of such disease states.

Other objects, features, benefits and advantages of the present invention will be apparent from this summary and the following descriptions of certain embodiments of such compounds, compositions and/or methods and will be readily apparent to those skilled in the art having knowledge of the synthetic techniques described herein. Such objectives, features, benefits and advantages will be apparent from the above as taken into conjunction with the accompanying examples, data, figures and references incorporated herein, together with all reasonable inferences to be drawn therefrom.

In part, the present invention can be directed to compounds of a formula

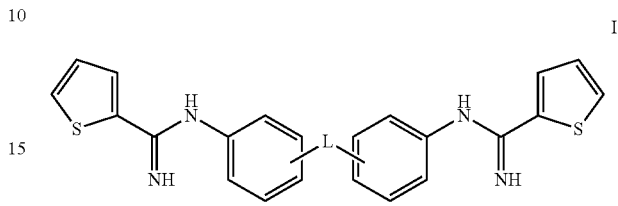

I wherein L can be a covalent bond or selected from divalent moieties such as but not limited to CH=CH, $CH_2CH_2$, $OCH_2CH(OH)$, $O(CH_2)_2O$, $O(CH_2)_3O$, $(CH_2)_2NH$, $(CH_2)_2NHCH_2$, $CH_2CH(CH_2NH_2)CH_2CH_2$, $CH_2CH(CH_2NH_2)NHCH_2$ and $OCH(CH_2NH_2)CH_2O$, together with salts, hydrates and/or solvates of such compounds.

Regardless of the identity of L, each phenyl moiety of such a compound can, independently, be substituted with a thiophene-2-carboximidamide moiety either meta or para with respect to such a linker moiety. In certain embodiments, such substituents can have a meta-relationship to such a linker and compounds can be of a formula

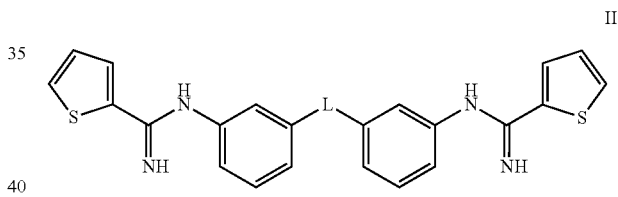

II wherein L can be selected from divalent linker moieties of the sort described above or referenced elsewhere herein.

In part, the present invention can also be directed to compounds of a formula

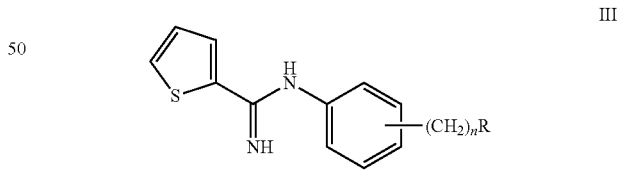

III wherein n can be an integer selected from 1 and 2; R can be selected from but not limited to

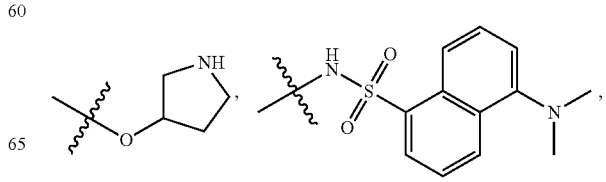

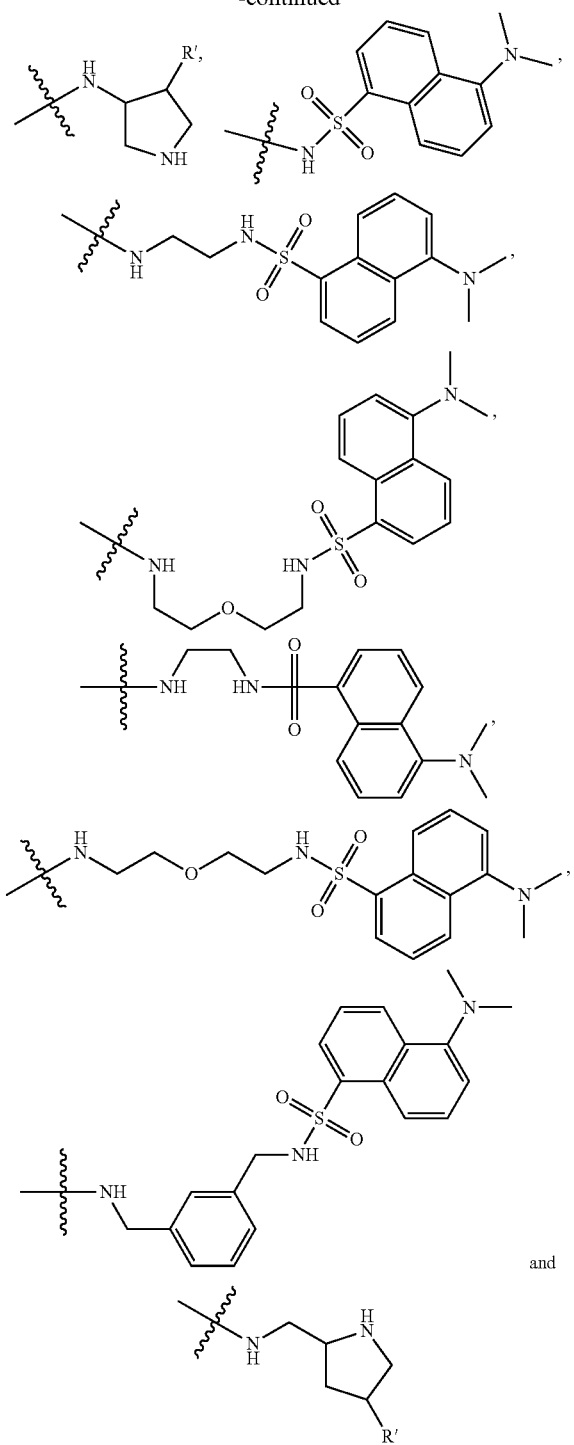
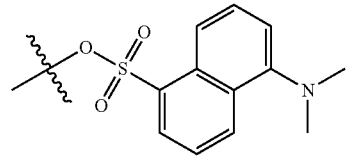
moieties; and R' can be selected from but not limited to
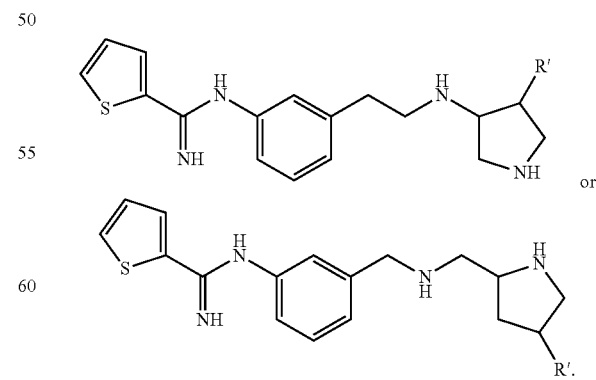
moieties, together with salts, hydrates and/or solvates of such compounds.
In certain embodiments, the phenyl moiety of such a compound can be meta-substituted. Regardless, such a compound can be of a formula
In part, the present invention can be directed to a compound selected from compounds of a formula

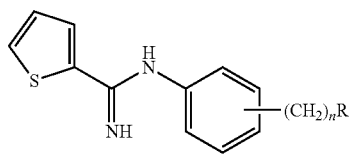

wherein n can be an integer selected from 1 and 2, R can be

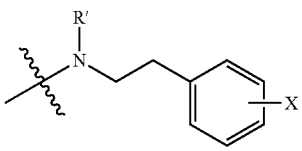

where R' can be selected from H, alkyl, arylalkyl, alkenyl, arylalkenyl, alkynyl and arylalkynyl moieties, and X can be selected from H, halogen, methyl, mono- and polyfluoro-substituted methyl moieties; and compounds of a formula

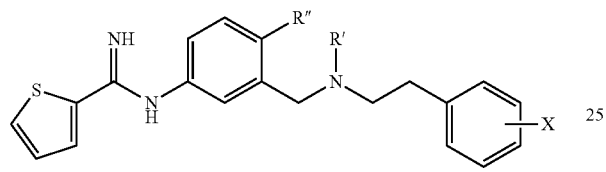

wherein R' can be selected from H, methylene, alkyl, arylalkyl, alkenyl, arylalkenyl, alkynyl, and arylalkynyl moieties, and R'' can be selected from H, a valence bond and a methylene moiety, providing that where R'' is a valence bond or a methylene moiety, R' can be a methylene moiety whereby R' and R'' taken together can form a 5-6 member heterocyclic ring, and X can be selected from H, halogen, methyl, mono- and polyfluorosubstituted methyl moieties; and salts thereof. While X is shown, above, to denote monosubstitution, the phenyl moiety can also be poly-substituted (e.g., $X_1$, $X_2$ and $X_3$, etc.) with one or a combination of such substituents.

In certain non-limiting embodiments, R'' can be H and such a compound can be of a formula

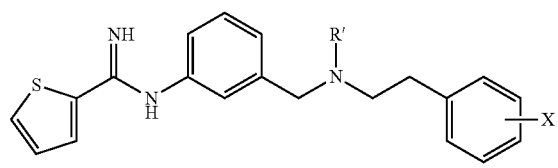

wherein R' and X can be as discussed above. Alternatively, in certain other embodiments, at least one of R' and R'' can be methylene, m can be 0 or 1, and such a compound can be of a formula

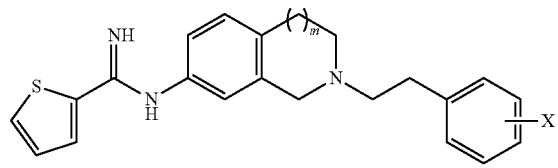

In part, the present invention can also be directed to compounds selected from compounds of a formula

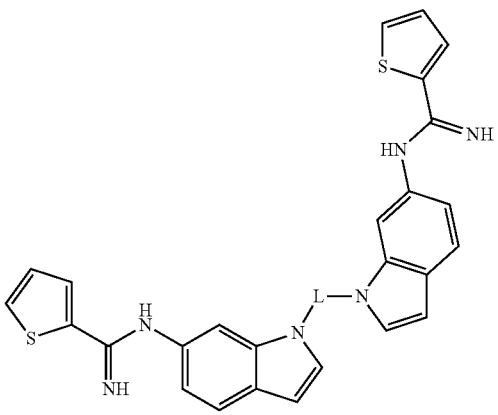

and compounds of a formula

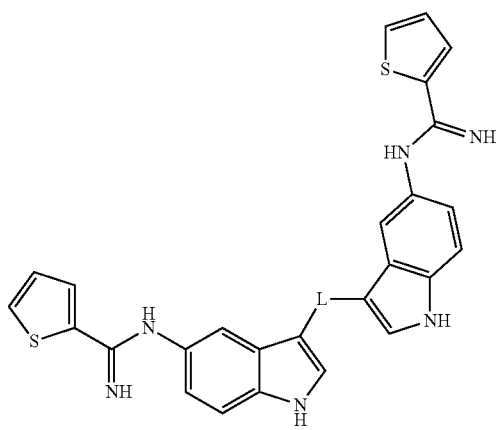

wherein, for each, L can be selected from divalent moieties of the sort discussed above or described elsewhere herein, together with salt, hydrates and/or solvates of such compounds. Without limitation, in certain such embodiments, for compounds of formula IV, L can be $CH_2CH_2$; and for compounds of formula V, L can be $CH(OH)CH(OH)$.

In part, the present invention can also be directed to compounds of a formula

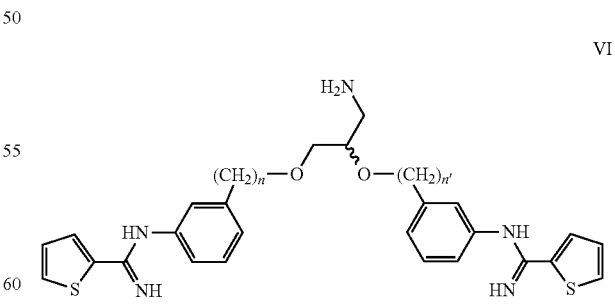

wherein n and n' can, independently, be an integer selected from 0 and 1, together with salts, hydrates and/or solvates of such compounds.

In part, the present invention can also be directed to compounds selected from compounds of a formula

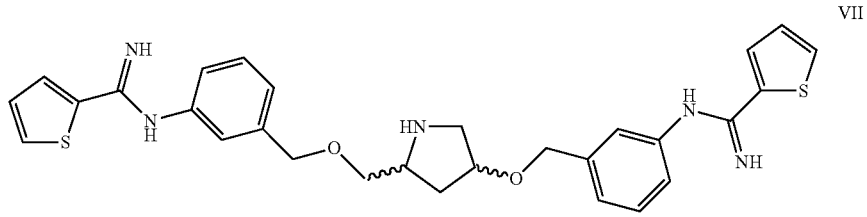 [SMILES: N=C(Nc1cccc(COCC2CC(OCc3cccc(NC(=N)c4cccs4)c3)CN2)c1)c1cccs1]

together with salts, hydrates and/or solvates of such compounds.

More generally, the present invention can also be directed to compounds selected from compounds of a formula

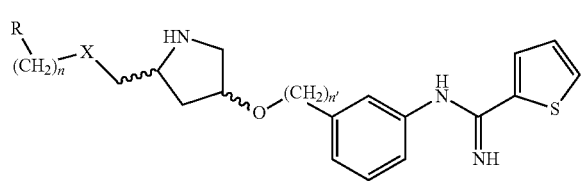

and compounds of a formula

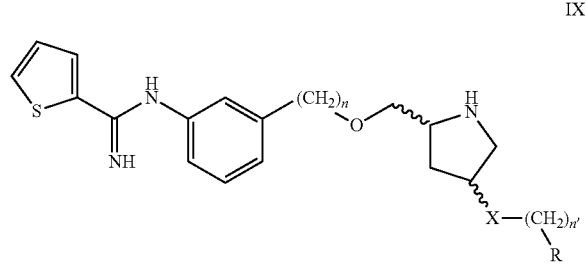

wherein, for each, n and n' can, independently, be an integer selected from 0 and 1; for each, X can be selected from O and NH; and, for each, R can be selected from but not limited to phenyl, fluoro-, chloro- and bromo- and thiophene-2-carboximidamide substituted phenyl moieties, whether having an ortho-, meta-, or para-relationship to the prolinyl linker moiety, together with salts, hydrates and/or solvates of such compounds.

In certain embodiments, X can be O. In certain such embodiments, n and n' can be 0. Regardless, R can be a thiophene-2-carboximidamide substituted phenyl moiety. Without limitation, such a compound can be present as a trans stereoisomer. In certain other such embodiments, n and n' can be 1. Regardless, R can be a thiophene-2-carboximidamide-substituted phenyl moiety. Such a compound can be selected from the cis and trans stereoisomers.

The present compounds and, in particular the compounds of formulae VI-VIII, are without stereochemical limitation. Where such compounds and/or their intermediates are available as racemic mixtures, the respective isomers can be resolved. Likewise, as certain such compounds are diastereomers, the corresponding enantiomers can be separated. Accordingly, any such stereocenter can be (S) or (R) with respect to any other stereocenter(s). Regardless of stereochemistry, in certain embodiments, a compound of this invention can comprise a primary, secondary and/or tertiary amine and can be present as an acid salt, either partially or fully protonated. In certain such embodiments, a counter ion(s) can be a conjugate base of a protic acid. Whether or not a salt, one or more such compounds can be utilized as a component of a pharmaceutical composition, optionally together with a pharmaceutically-acceptable carrier component.

In part, the present invention can also provide a method of modulating or affecting activity of inhibiting a nitric oxide synthase, such a method comprising contacting a nitric oxide synthase with an effective amount of any one or more of the present compounds, including, but not limited to those illustrated by the following examples, referenced figures and/or accompanying synthetic schemes. Such a method can comprise providing a compound or a related composition of this invention; and contacting a nitric oxide synthase enzyme with such a compound/composition, such contact as can selectively inhibit neuronal nitric oxide synthase over inducible and/or endothelial isoforms.

DETAILED DESCRIPTION OF CERTAIN EMBODIMENTS OF THE INVENTION

Figure 1:
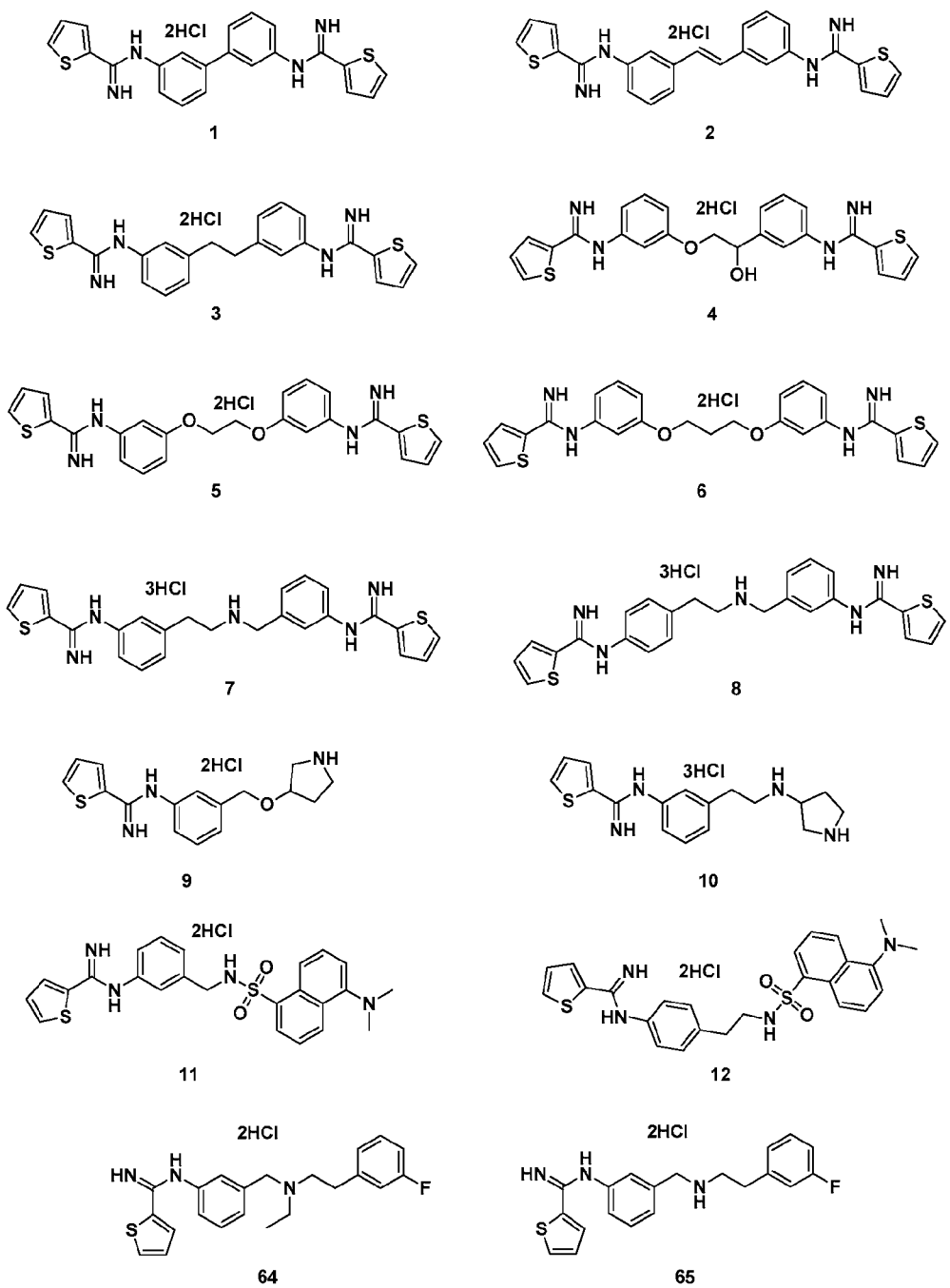
FIG. 1. Chemical structures of representative, non-limiting inhibitor compounds, in accordance with certain embodiments of this invention.

Without limitation, in accordance with broader aspects of this invention, various compounds of this invention can be prepared as schematically illustrated, below. In particular, selective nNOS inhibitor compounds of this invention can be prepared using synthetic techniques common to the chemical literature and well-known to those skilled in the art. For instance, without limitation, a synthetic route for target molecule 1 (FIG. 1) is shown in Scheme 1. Homo-coupling reaction of 1-iodo-3-nitrobenzene gave 26 in a moderate yield. The nitro groups of 26 were reduced to amino groups in a quantitative yield, then a coupling reaction with methyl thiophene-2-carbimidothioate hydroiodide salt was used to generate final product 1.

Scheme 1.

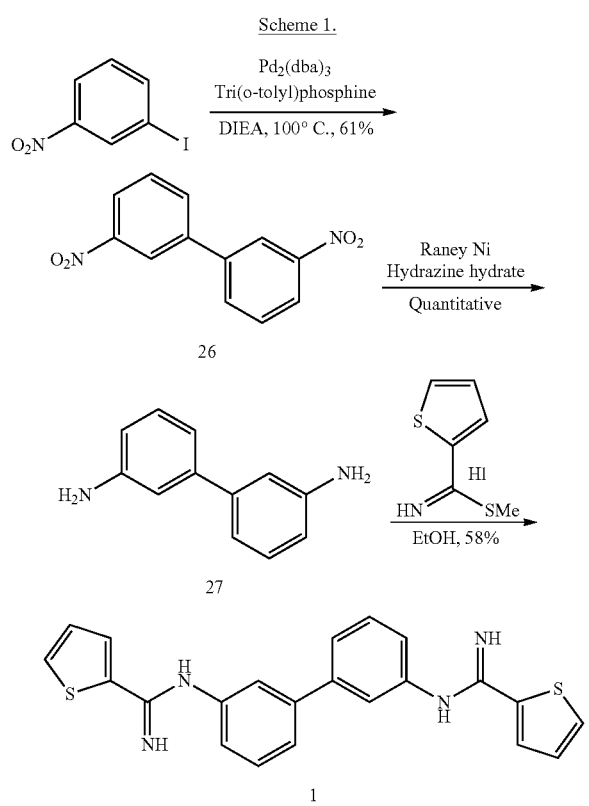

A synthetic route for target molecules 2 and 3 (FIG. 1) is shown in Scheme 2. A Wittig reaction of 3-nitrobenzaldehyde with corresponding phosphorus glide of 1-(bromomethyl)-3-nitrobenzene allowed the isolation of the intermediate alkene in an 87% yield. The nitro groups of 29 were reduced to amino groups in a quantitative yield, and then a coupling reaction with methyl thiophene-2-carbimidothioate hydroiodide salt was used to generate final product 2. Catalytic hydrogenation of 2 reduced the double bond, giving final product 3 in a high yield.

Scheme 2.

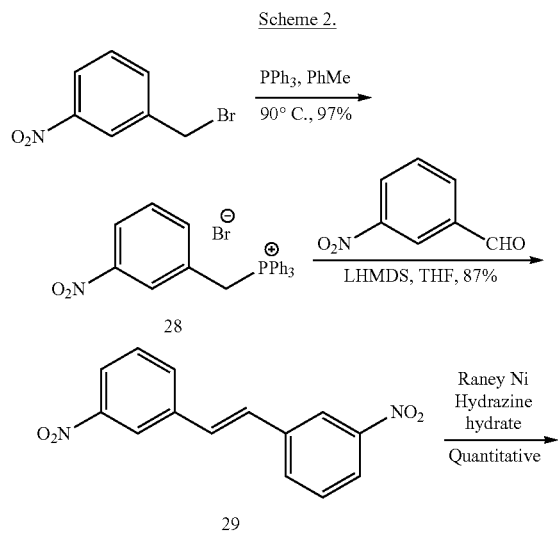

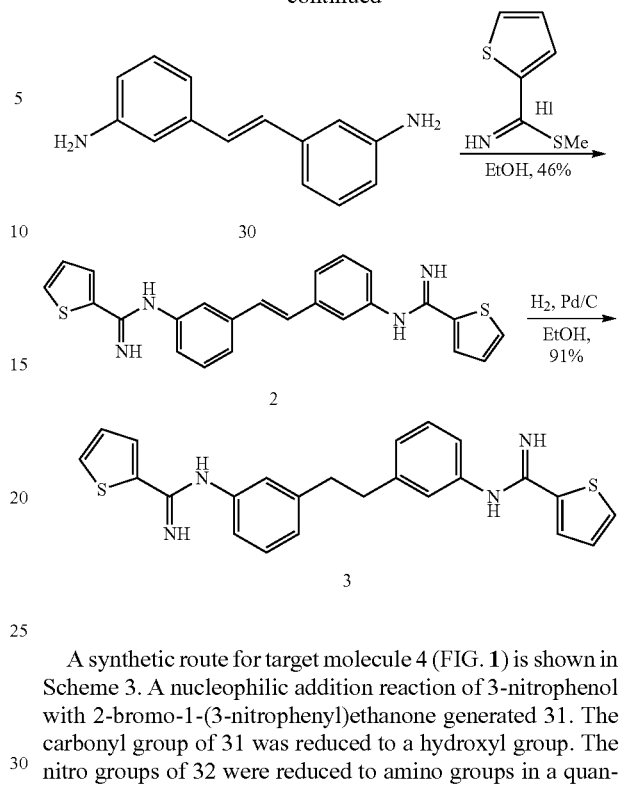

A synthetic route for target molecule 4 (FIG. 1) is shown in Scheme 3. A nucleophilic addition reaction of 3-nitrophenol with 2-bromo-1-(3-nitrophenyl)ethanone generated 31. The carbonyl group of 31 was reduced to a hydroxyl group. The nitro groups of 32 were reduced to amino groups in a quantitative yield, and then a coupling reaction with methyl thiophene-2-carbimidothioate hydroiodide salt was used to generate final product 4.

Scheme 3.

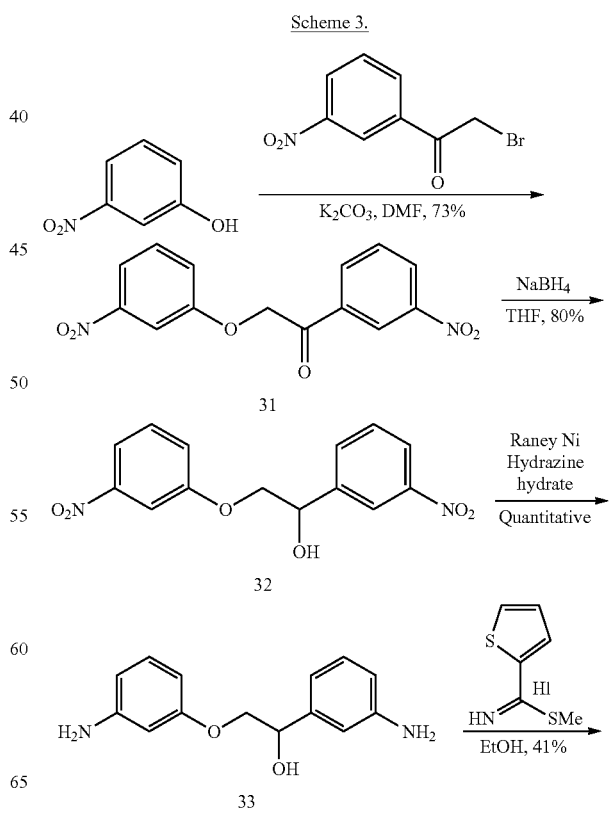

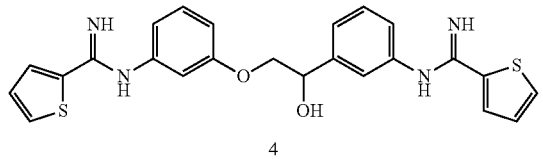

4

A synthetic route for target molecules 5 and 6 (FIG. 1) is shown in Scheme 4. Nucleophilic addition reactions of 3-nitrophenol with corresponding alkyl halides generated 34 and 35. The nitro groups of 34 and 35 were reduced to amino groups in quantitative yields, and then coupling reactions with methyl thiophene-2-carbimidothioate hydroiodide salt were used to generate final products 5 and 6, respectively.

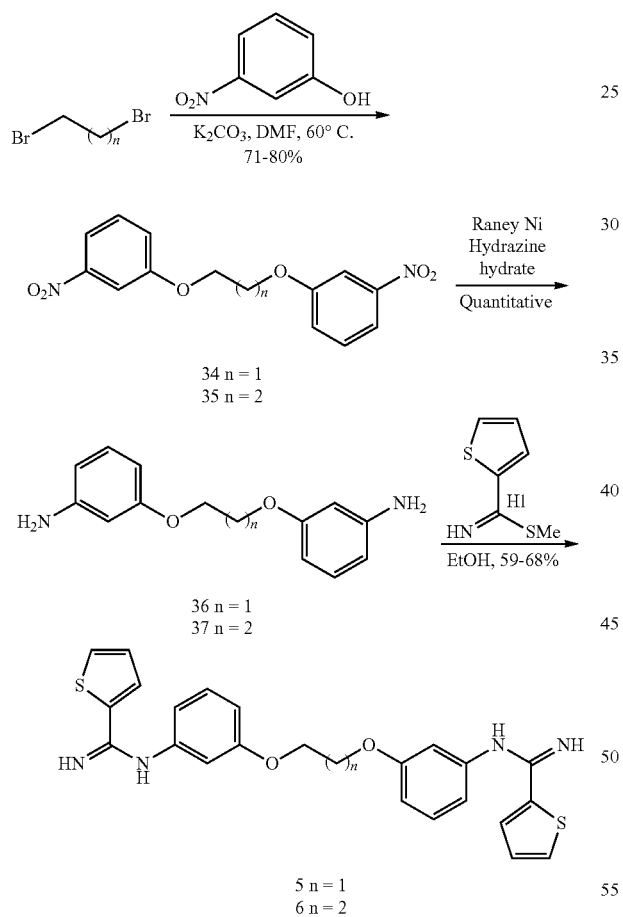

A synthetic route for target molecules 7 and 8 (FIG. 1) is shown in Scheme 5. Reductive amination of 3-nitrobenzaldehyde with corresponding amines generated 38 and 39. The amino groups of 38 and 39 were protected by Boc group. The nitro groups of 40 and 41 were reduced to amino groups in quantitative yields, and then coupling reactions with methyl thiophene-2-carbimidothioate hydroiodide salt were used to generate intermediates 44 and 45, respectively. Deprotection of the Boc groups generated 7 and 8.

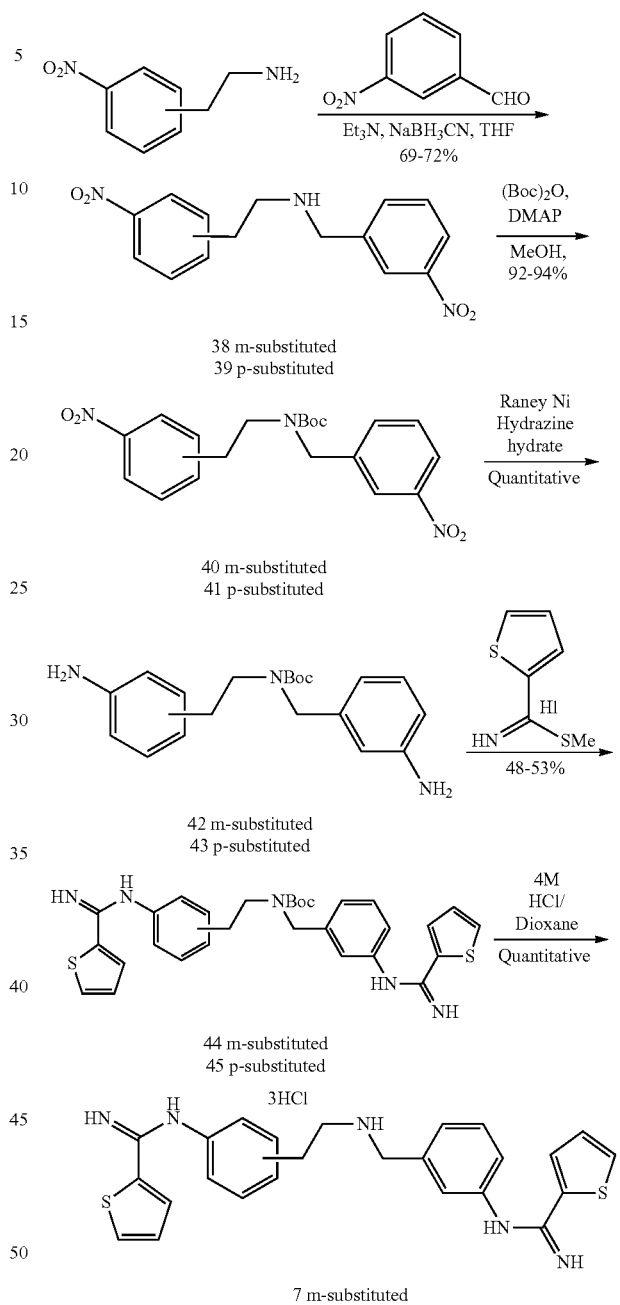

Figure 5:
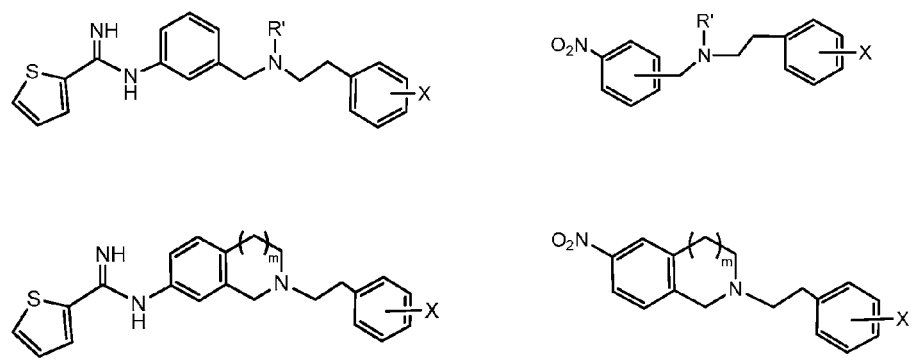
FIG. 5. Chemical structures of non-limiting inhibitor compounds and corresponding synthetic intermediates, in accordance with certain embodiments of this invention.

A synthetic route for target molecule 9 (FIG. 1) is shown in Scheme 6. tert-Butyl 3-hydroxypyrrolidine-1-carboxylate was treated with NaH, and resulting anion was allowed to react with 1-(bromomethyl)-3-nitrobenzene, giving ether 46 in a yield of 76%. The nitro group of 46 was reduced to amino group in quantitative yield, and then coupling reaction with methyl thiophene-2-carbimidothioate hydroiodide salt was used to generate intermediate 48. Deprotection of the Boc group generated final product 9. Analogously, as illustrated in Scheme 6, various other nitrobenzene intermediates can be prepared en route to the corresponding thiophene-2-carboximidamide. (See, e.g., FIG. 5.)

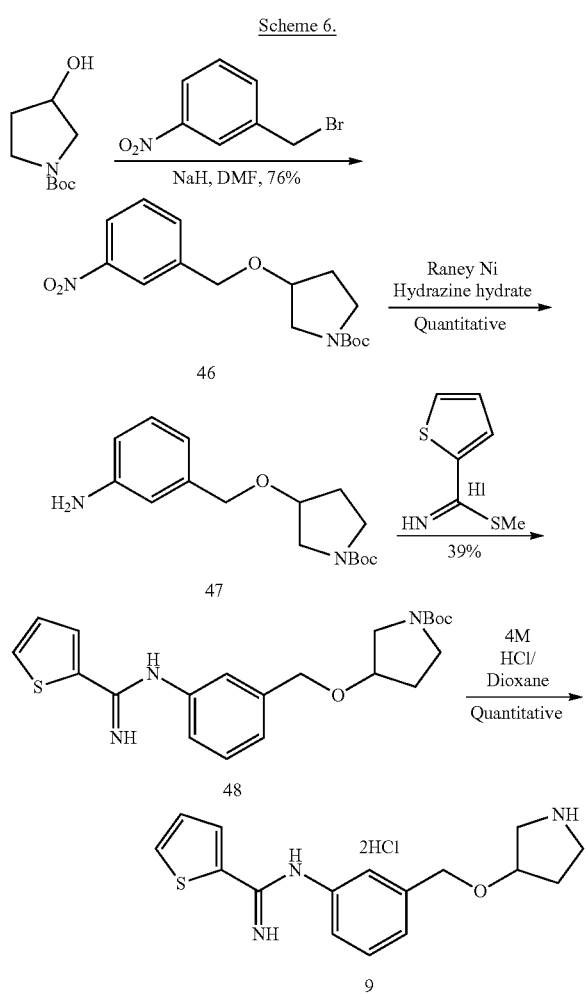

A synthetic route for target molecule 10 (FIG. 1) is shown in Scheme 7. The hydroxyl group of tert-Butyl 3-hydroxy-pyrrolidine-1-carboxylate was oxidized to aldehyde 49 with IBX, and then a reductive amination with corresponding amine was used to generate 50. The amino group of 50 was protected by Boc group. The nitro group of 51 was reduced to amino group in quantitative yield, and then coupling reaction with methyl thiophene-2-carbimidothioate hydroiodide salt was used to generate intermediate 52. Deprotection of the Boc groups generated final product 10.

A synthetic route for target molecules 11 and 12 (FIG. 1) is shown in Scheme 8. Selected amines were subjected to amidation with dansyl chloride to afford corresponding intermediates 54 and 55. The nitro groups of 56 and 57 were reduced to amino groups in quantitative yields, and then coupling reactions with methyl thiophene-2-carbimidothioate hydroiodide salt were used to generate final products 11 and 12.

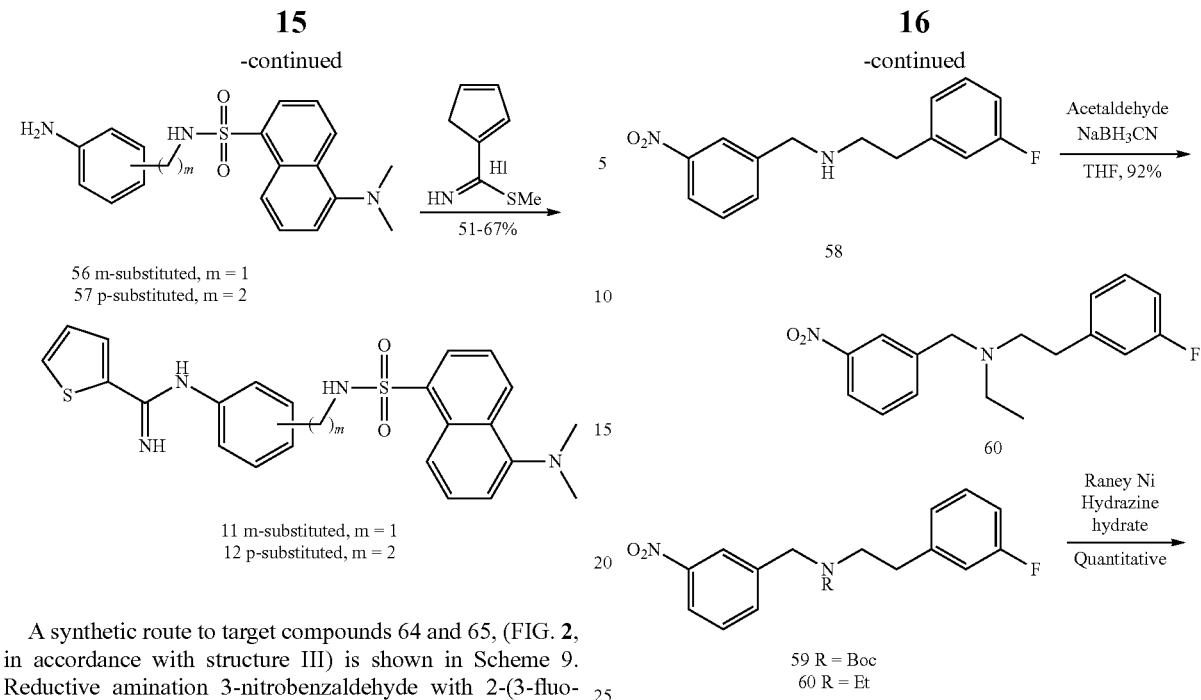

56 m-substituted, m = 1
57 p-substituted, m = 2

11 m-substituted, m = 1
12 p-substituted, m = 2

Figure 2A:
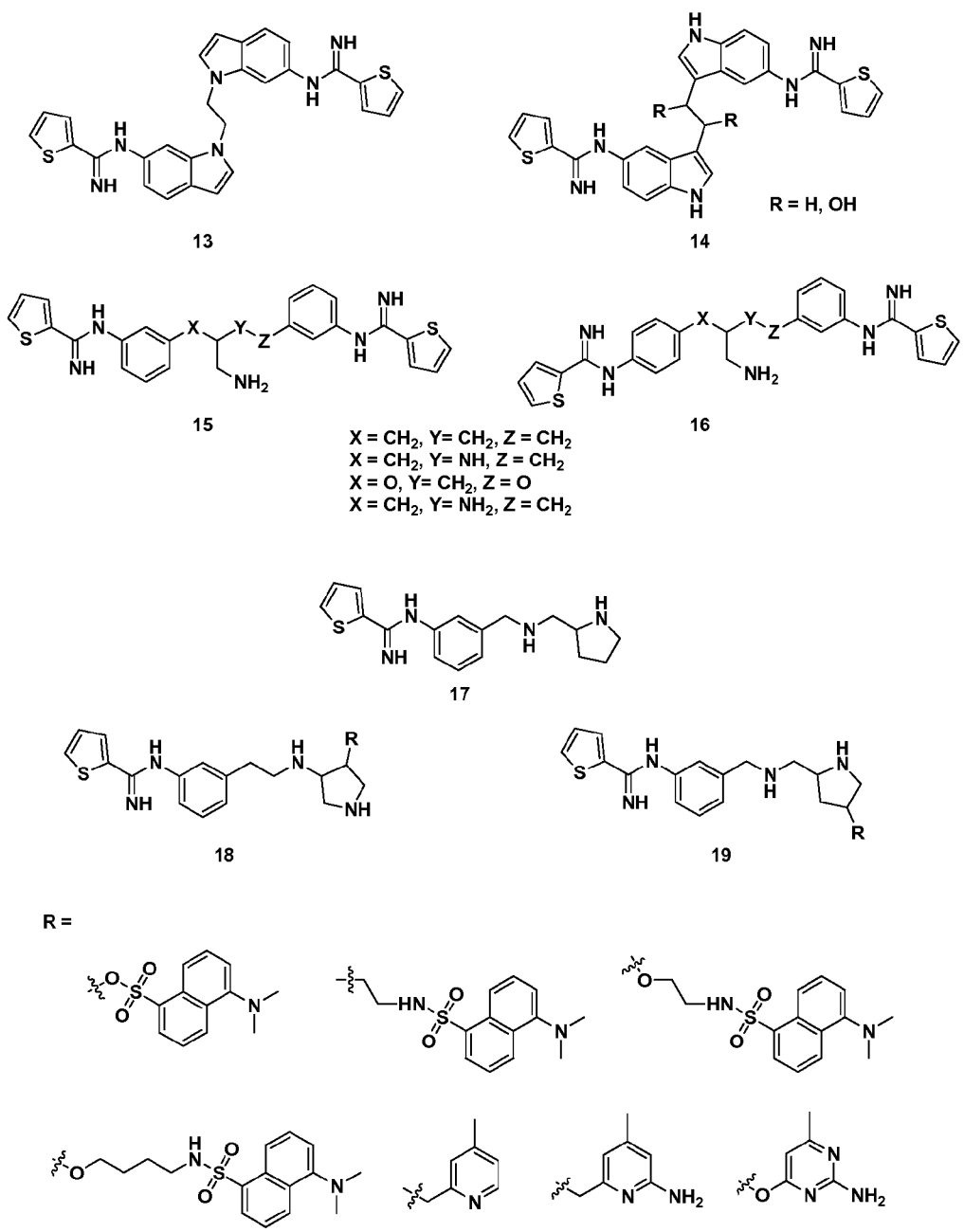
FIGS. 2A-B. Representative schematic chemical structures of non-limiting selective nNOS inhibitors compounds, in accordance with certain embodiments of this invention.
Figure 2B:
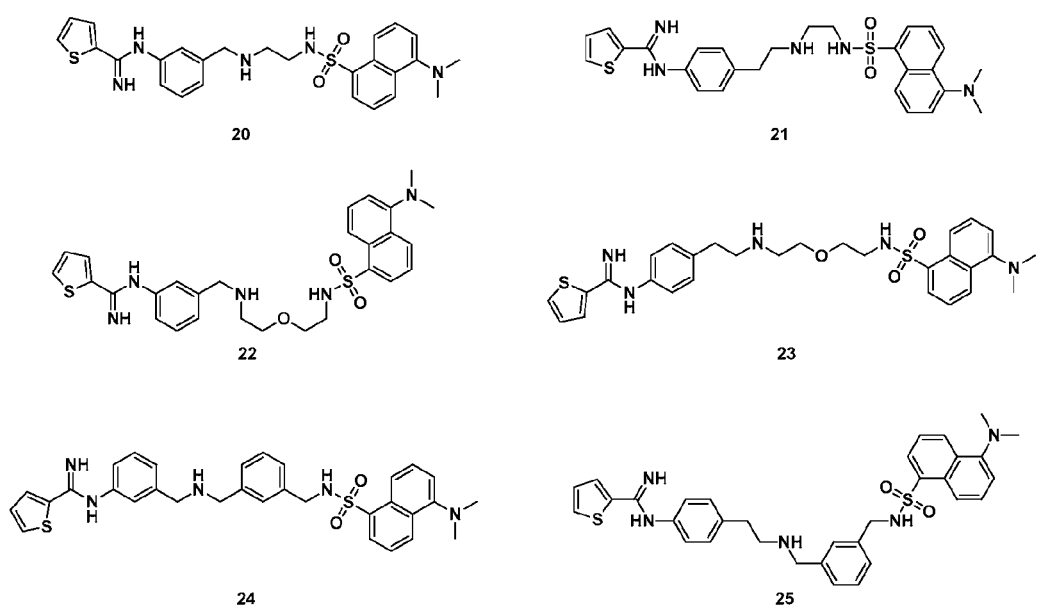

A synthetic route to target compounds 64 and 65, (FIG. 2, in accordance with structure III) is shown in Scheme 9. Reductive amination 3-nitrobenzaldehyde with 2-(3-fluorophenyl)ethanamine generated intermediate 58. Alternatively, the amino group of 58 was protected with Boc and ethyl groups. Nitro group reduction and coupling with methyl thiophene-2-carbimidothioate hydroiodide salt were performed under conditions similar to those adopted for the synthesis of compound 1 (e.g., Scheme 1), giving intermediate 63 and target product 64, respectively. Deprotection of the Boc group of 63 generated final product 65.

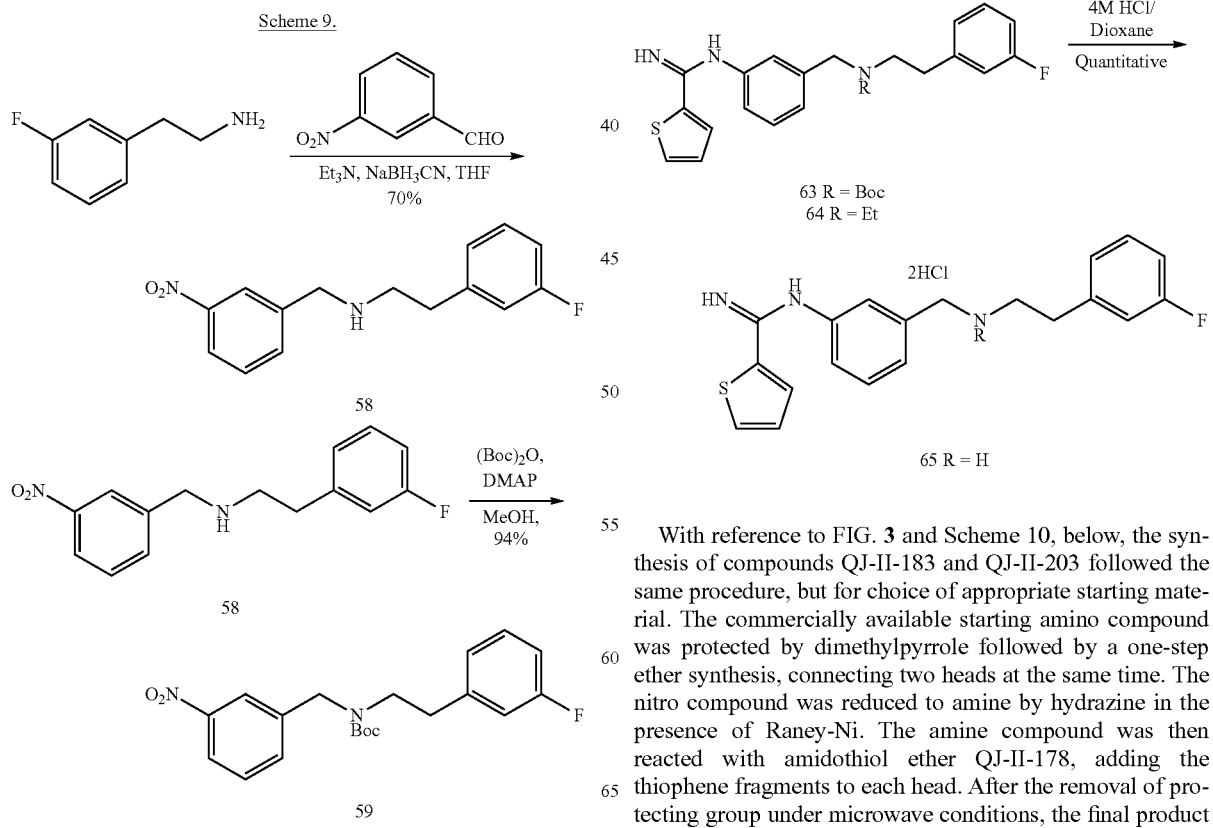

Figure 3:
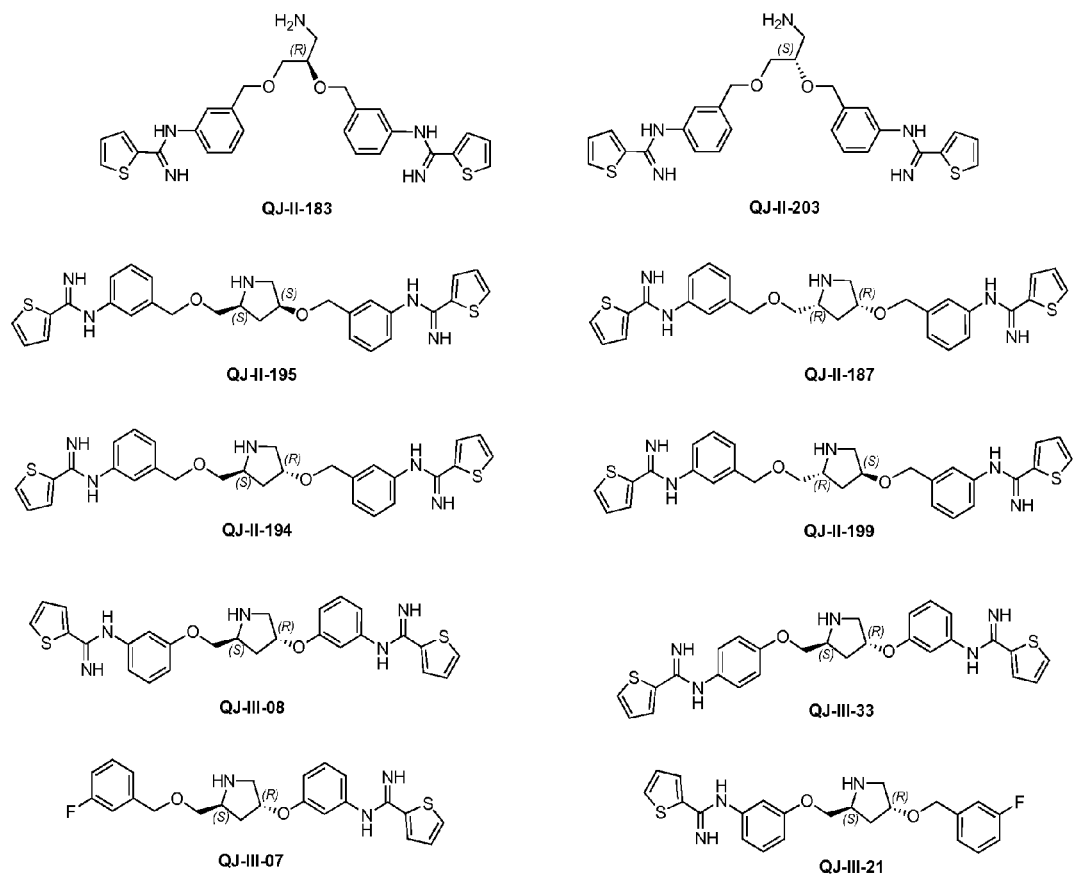
FIG. 3. Chemical structures of representative, non-limiting inhibitor compounds, in accordance with certain embodiments of this invention.

With reference to FIG. 3 and Scheme 10, below, the synthesis of compounds QJ-II-183 and QJ-II-203 followed the same procedure, but for choice of appropriate starting material. The commercially available starting amino compound was protected by dimethylpyrrole followed by a one-step ether synthesis, connecting two heads at the same time. The nitro compound was reduced to amine by hydrazine in the presence of Raney-Ni. The amine compound was then reacted with amidothiol ether QJ-II-178, adding the thiophene fragments to each head. After the removal of protecting group under microwave conditions, the final product was obtained in a 63% yield.

Scheme 10.

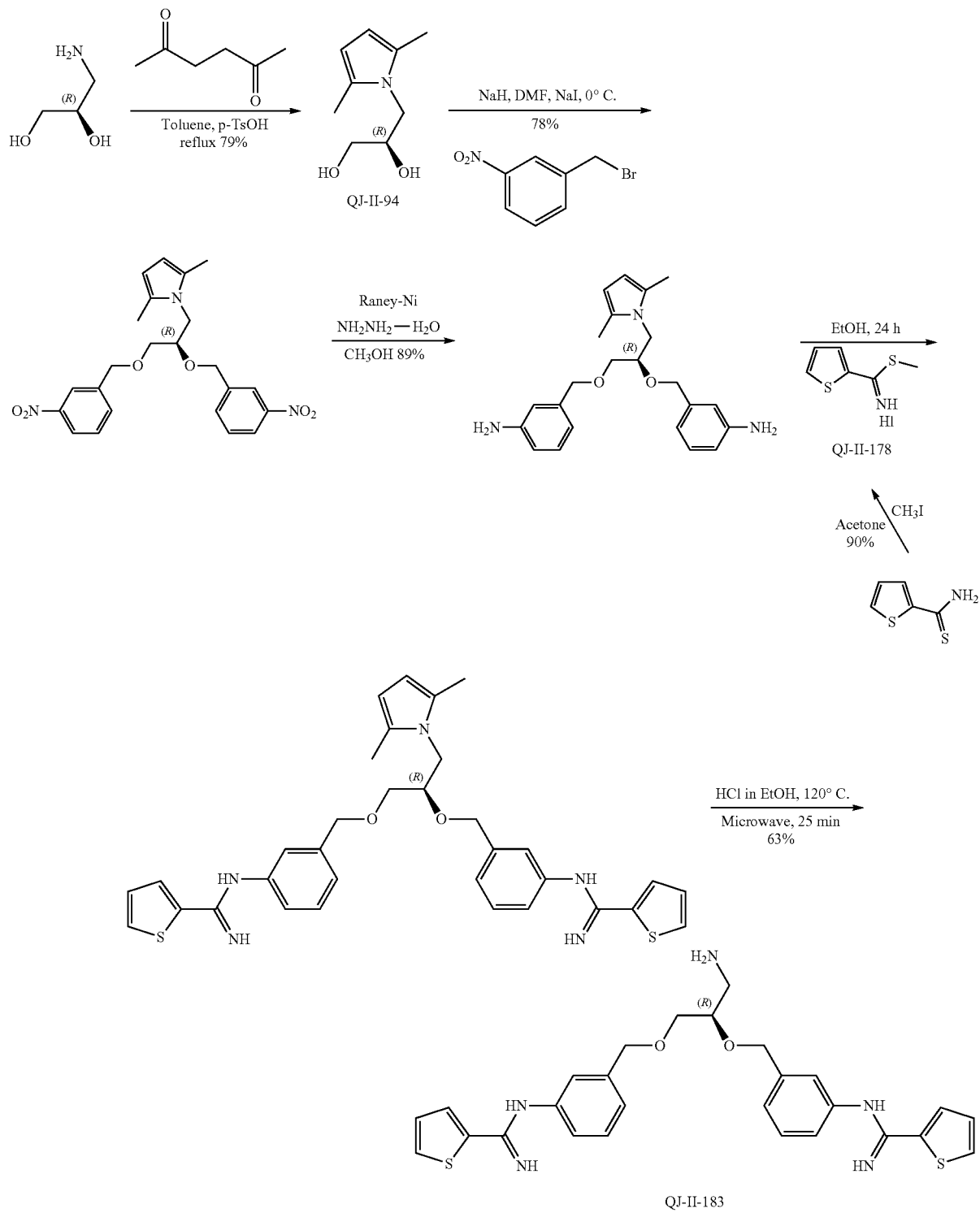

With reference to Scheme 11, the synthesis of compounds QJ-II-187, QJ-II-194, QJ-II-195 and QJ-II-199 followed the same procedure but for choice of appropriate starting material. The commercially available Boc-protected prolinyl analogue was reduced to the alcohol by LiBH$_4$ in a quantitative yield. Then, an ether synthesis linked the two heads via a one-step reaction. The nitro compound was reduced to amine by hydrazine in the presence of Raney-Ni in a 97% yield. The amine compound was then reacted with amidothiol ether QJ-II-178, adding the thiophene fragments to each head. The final product was obtained in a quantitative yield after removing the Boc protecting group under acidic conditions.

Scheme 11.

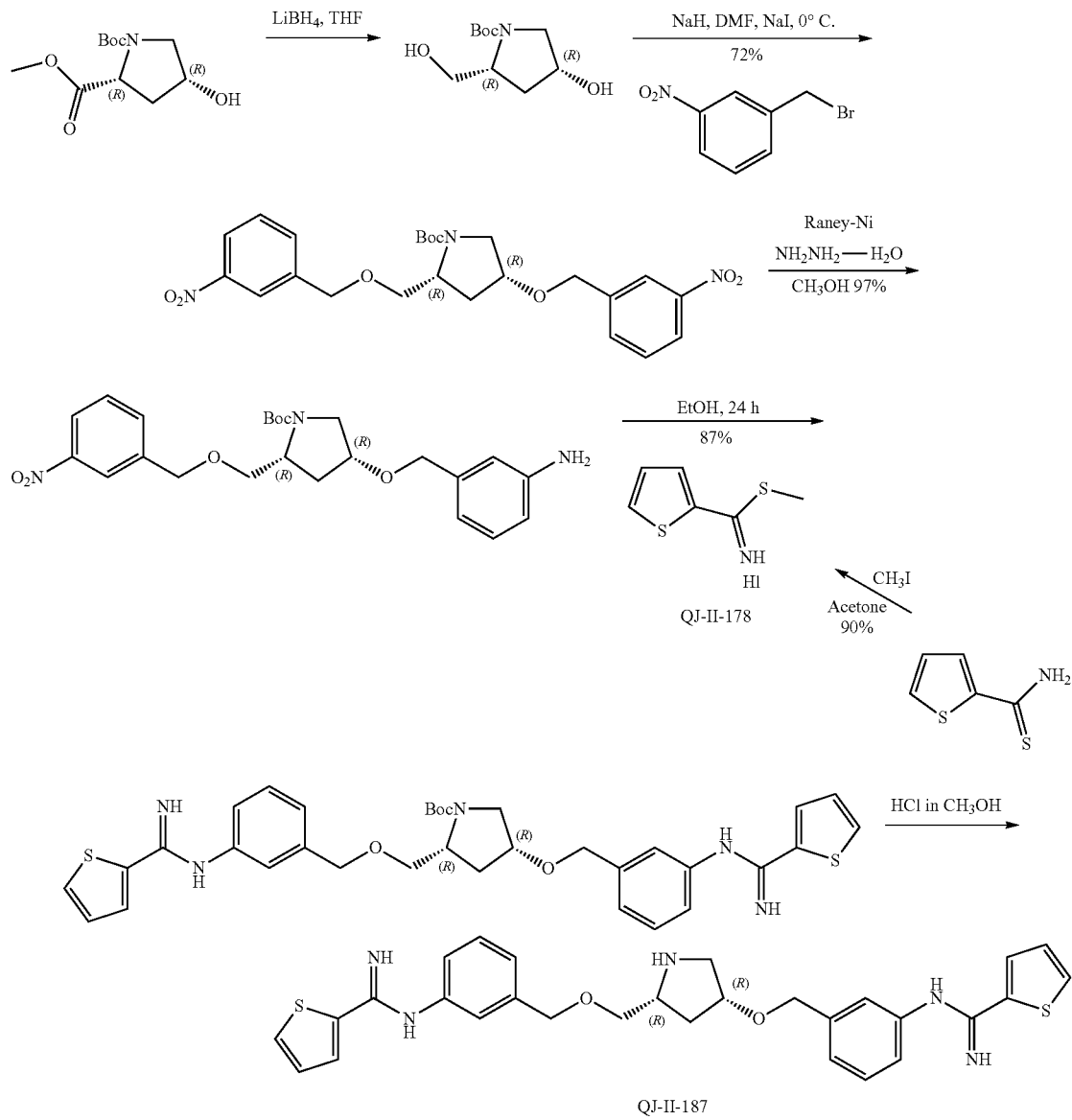

With reference to Scheme 12, the synthesis of QJ-III-08 (FIG. 3) begins with a Mitsunobu reaction, coupling the first nitrophenyl group to the prolinyl linker moiety. After reducing the methyl ester to an alcohol with LiBH₄, the second nitrophenyl group was coupled via a second Mitsunobu reaction. Upon Raney-Ni and hydrazine reduction of the nitro groups, the resulting compound was ready to react with amidothiol ether QJ-II-178 to provide the double-headed thiophene scaffold. The final compound was obtained after removal of the Boc protecting group.

Scheme 12.

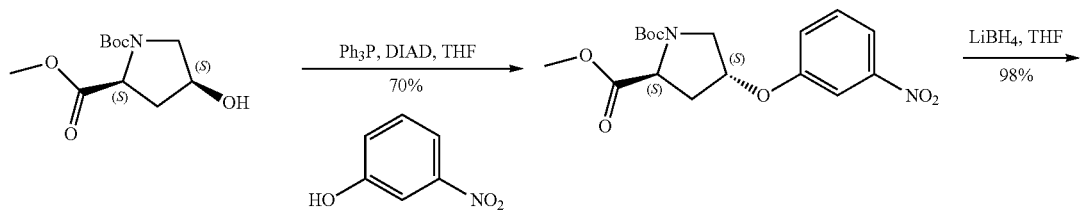

-continued

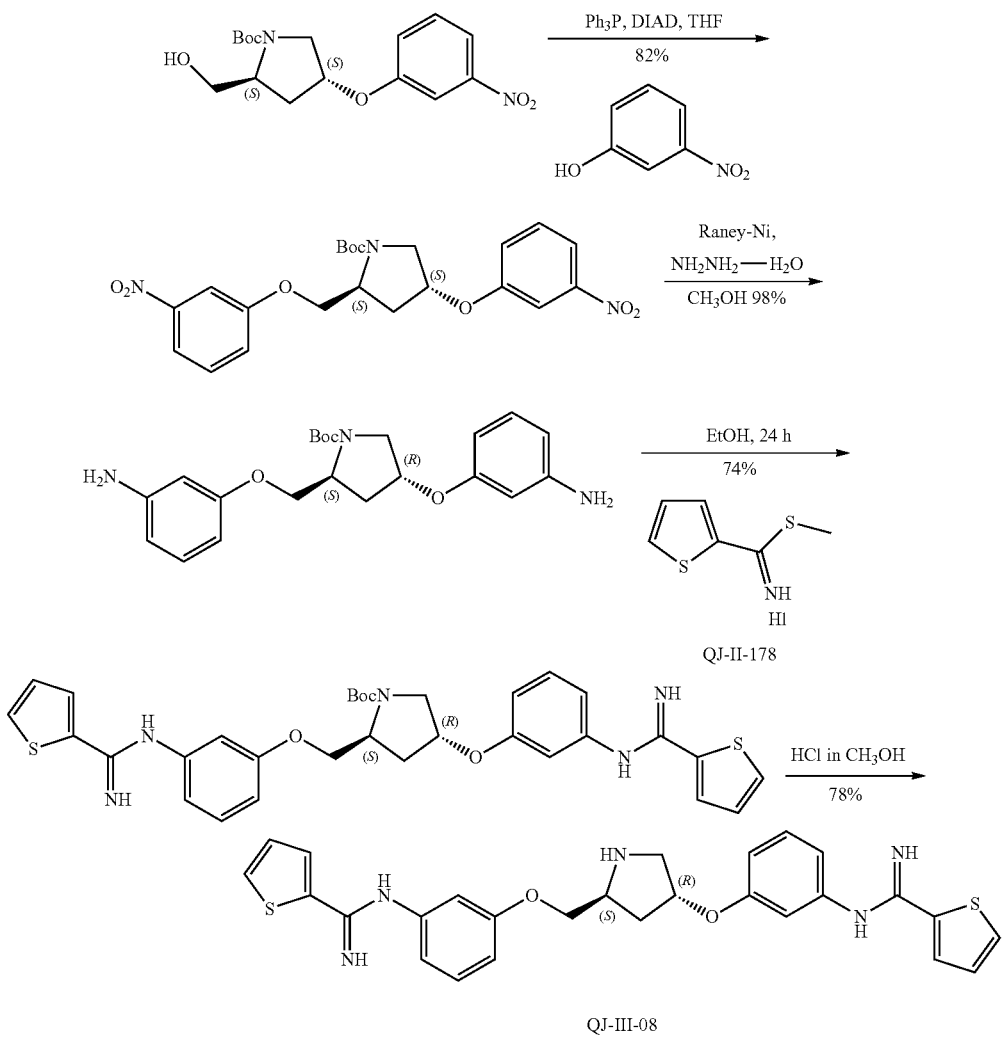

QJ-II-178

QJ-III-08

Compound QJ-III-33 (FIG. 3) is very similar to QJ-III-08, but for para-substitution of the second thiophene head (instead of meta-substitution) with respect to the linker moiety. With reference to Scheme 13, the same first two steps of the QJ-III-08 synthesis are employed, but the second Mitsunobu reaction uses para-substituted nitrophenol. The remaining synthetic steps follow those for QJ-III-08 with comparable yields.

Scheme 13.

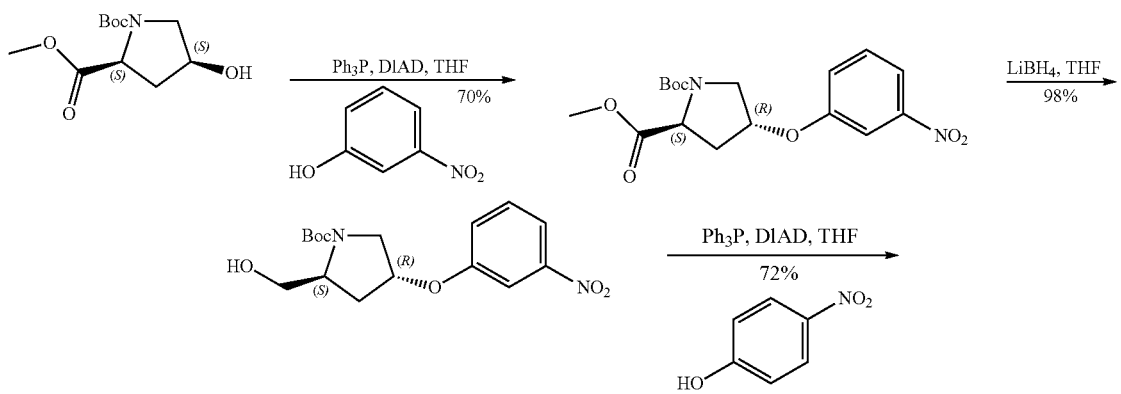

-continued

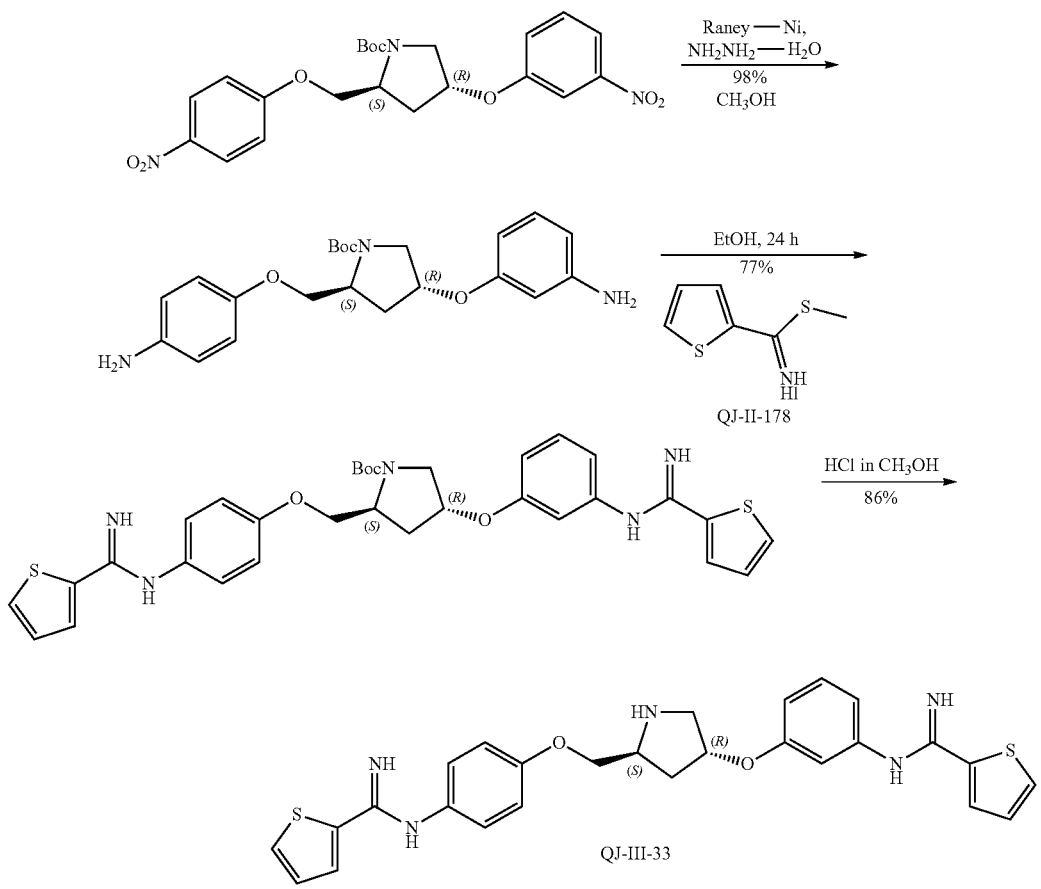

With reference to Scheme 14, the synthesis of compound QJ-III-07 shares a key intermediate with that of the two target compounds of Schemes 12 and 13; that is, meta-substituted nitrophenyl alcohol. However, instead of a Mitsunobu reaction, an ether synthesis was used to couple the fluorobenzyl group to the prolinyl linker moiety. The resulting compound was reacted with amidothiol ether QJ-II-178 to provide the asymmetric double-headed scaffold. With the removal of the Boc protecting group, the final compound was obtained in 85% yield.

Scheme 14.

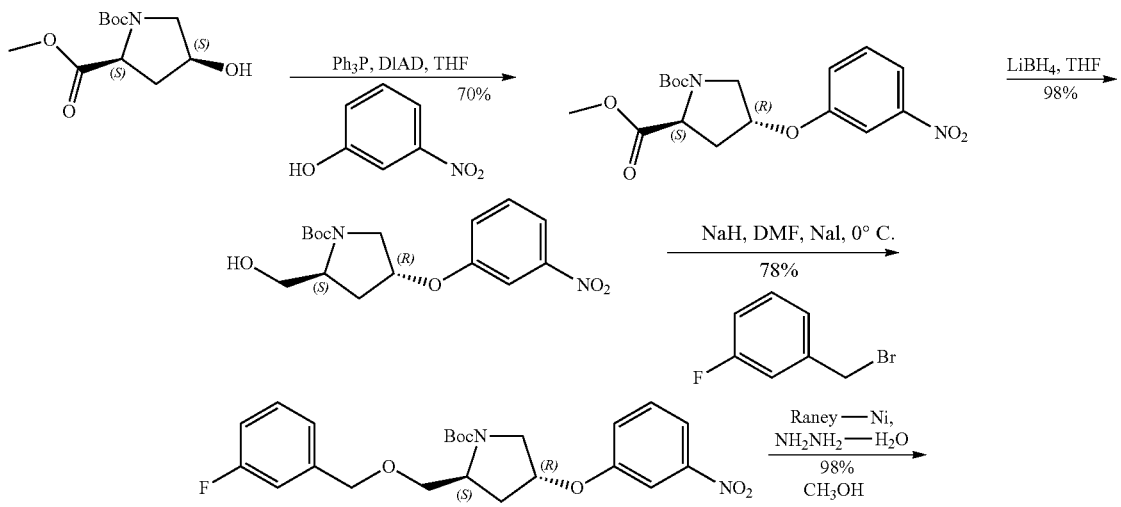

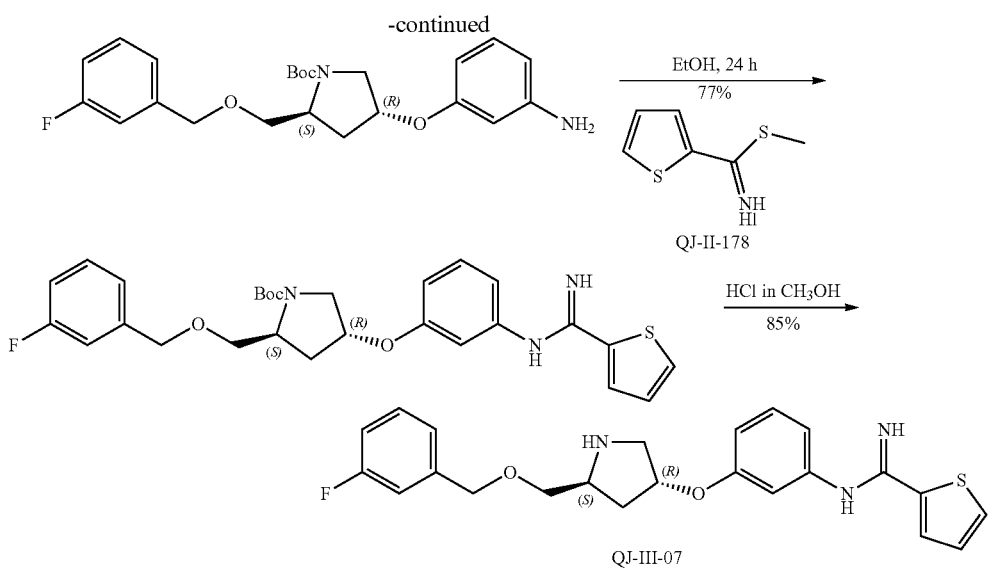

Compound QJ-III-21 is similar in structure to QJ-III-07 (see, FIG. 3), but for transposition of the two opposed head groups. With reference to Scheme 15, coupling of the fluorobenzyl group to the prolinyl linker via an ether synthesis is achieved before Mitsunobu reaction with the nitrophenyl group. The remaining synthetic steps are the same as employed for QJ-III-07, with similar yields.

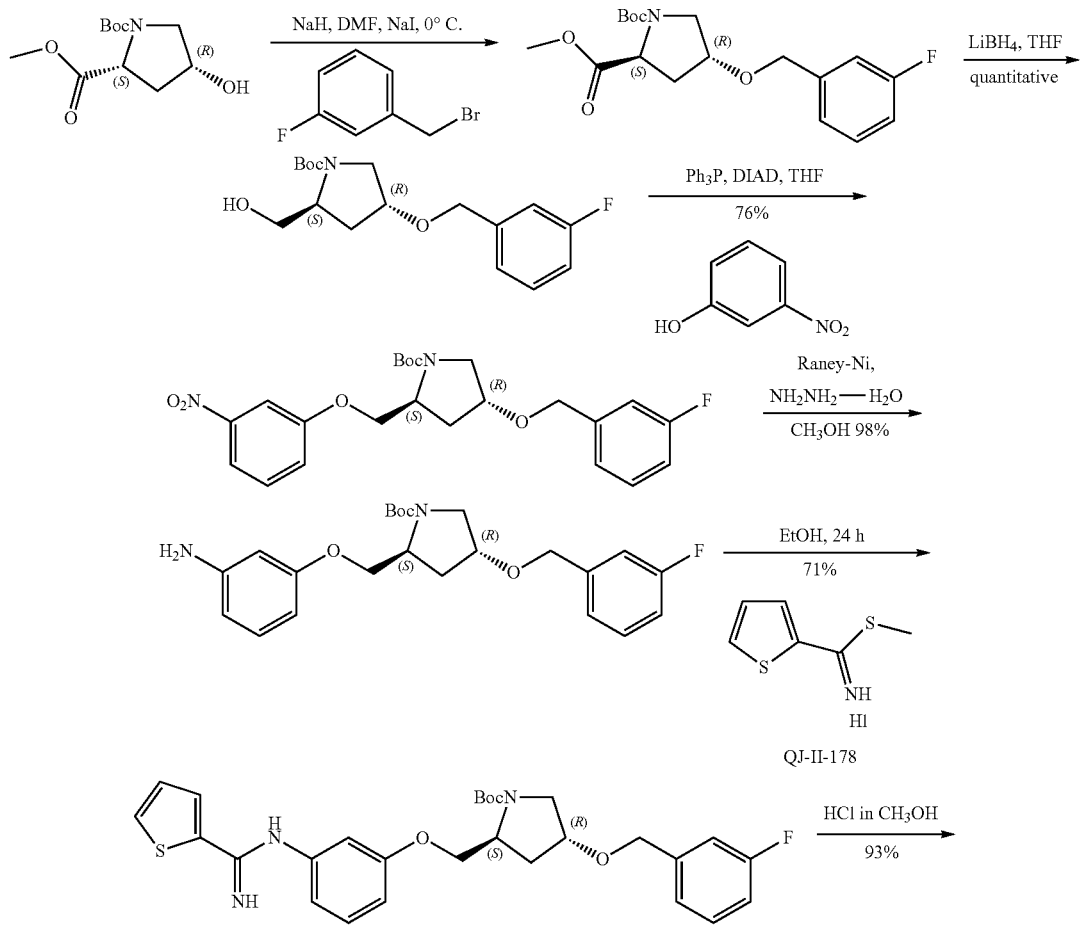

-continued

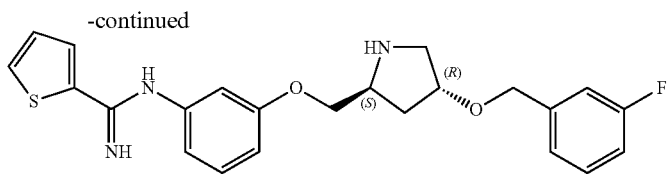

QJ-III-21

With respect to either of the compounds, compositions and/or methods of the present invention, such compounds or moieties thereof can suitably comprise, consist of or consist essentially of any of the respective aforementioned moieties and/or substituents thereof. Each such compound or moiety/substituent thereof is compositionally distinguishable, characteristically contrasted and can be practiced in conjunction with the present invention separate and apart from another. Accordingly, it can also be understood that the inventive compounds, compositions and/or methods, as illustratively enclosed disclosed herein, can be practiced or utilized in the absence of any one compound, moiety and/or substituent, such compound, moiety, and/or substituent which may or may not be disclosed, referenced or inferred herein, the absence of which may not be specifically disclosed, referenced or inferred herein.

The present invention can also, as would be understood by those skilled in the art, be extended to or include methods using or in conjunction with a pharmaceutical composition comprising a compound of the sort described herein and a physiologically or otherwise suitable formulation. In some embodiments, the present invention includes one or more NOS inhibitors, as set forth above, formulated into a composition together with one or more physiologically tolerable or acceptable diluents, carriers, adjuvants or vehicles that are collectively referred to herein as carriers. Compositions suitable for NOS contact or administration can comprise physiologically acceptable sterile aqueous or nonaqueous solutions, dispersions, suspensions or emulsions. The resulting compositions can be, in conjunction with the various methods described herein, for administration or contact with a human/mammalian nitric oxide synthase expressed or otherwise present therein. Whether or not in conjunction with a pharmaceutical composition, "contacting" means that a nitric oxide synthase and one or more inhibitor compounds of this invention are brought together for purpose of binding and/or complexing such a compound to the enzyme. Amounts of a compound effective to inhibit a nitric oxide synthase may be determined empirically, and making such determinations is within the skill in the art. Inhibition or otherwise affecting or modulating nitric oxide synthase activity includes both reduction and/or mitigation, as well as elimination of NOS activity and/or nitric oxide production.

It is understood by those skilled in the art that dosage amount will vary with the activity of a particular inhibitor compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more neuronal nitric oxide synthase inhibitor compounds for the manufacture of a medicament for therapeutic use in the treatment of human disease states implicating NOS activity and/or nitric oxide production, including but not limited to the treatment of neurodegenerative diseases.

Figure 4:
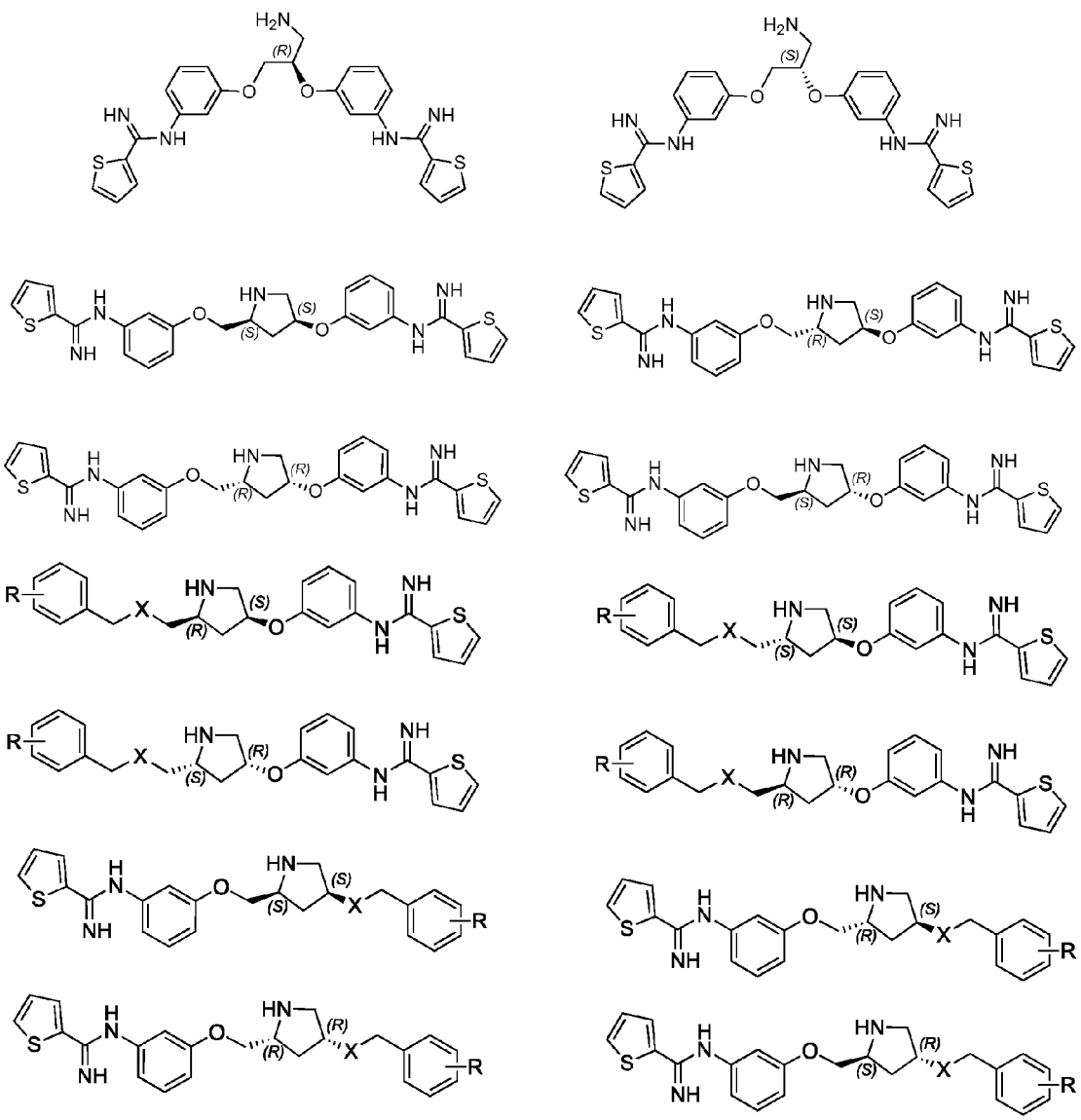
FIG. 4. Representative schematic chemical structures of non-limiting selective nNOS inhibitor compounds in accordance with certain embodiments of this invention.

In accordance with this invention, various other compounds can be prepared using synthetic techniques of the sort described herein or straight forward modifications thereof, such modifications as would be understood by those skilled in the art made aware of this invention, such compounds, techniques and/or modifications limited only by commercially- or synthetically-available starting materials and reagents. (See, e.g., FIGS. 2 and 4.)

EXAMPLES OF THE INVENTION

The following non-limiting examples and data illustrate various aspects and features relating to the compounds and/or methods of the present invention, including the characterization and testing of various selective inhibitor compounds, as are available through the synthetic methodologies described herein. In comparison with the prior art, the present compounds provide results that are surprising, unexpected and contrary thereto. While the utility of this invention is illustrated through the use of several non-limiting compounds, moieties thereof and substituents thereto, it will be understood by those skilled in the art that comparable results are obtainable with various other compounds, moieties and/or substituents, as are commensurate with the scope of this invention.

Example 1

With reference to FIG. 1 and schemes 1-9, compounds I-12 and 64-65 were characterized as provided below.

Example 1a

N,N'-([1,1'-biphenyl]-3,3'-diylbis(thiophene-2-carboximidamide) (1)

$^1$H NMR (500 MHz, DMSO-d6): δ 8.24-8.16 (m, 4H), 7.90-7.80 (m, 4H), 7.70 (t, J=8.0 Hz, 2H), 7.51 (d, J=4.5 Hz, 2H), 7.45-7.38 (m, 2H). $^{13}$C NMR (125 MHz, DMSO-d6): δ

156.61, 140.59, 135.37, 134.96, 134.59, 130.65, 129.07, 128.62, 126.63, 125.25, 124.12.

Example 1b (E)-N,N'-(ethane-1,2-diylbis(3,1-phenylene))bis(thiophene-2-carboximidamide) (2)

$^1$H NMR (500 MHz, MeOD): δ 8.09 (t, J=5.0 Hz, 4H), 7.59-7.27 (m, 10H), 6.82 (s, 2H). $^{13}$C NMR (125 MHz, MeOD): δ 159.37, 140.56, 135.90, 135.61, 135.31, 131.57, 131.34, 130.60, 130.02, 127.33, 125.89.

Example 1c

N,N'-(ethane-1,2-diylbis(3,1-phenylene))bis(thiophene-2-carboximidamide) (3)

$^1$H NMR (500 MHz, MeOD): δ 8.17-8.02 (m, 4H), 7.56-7.51 (t, J=7.5 Hz, 2H), 7.45-7.38 (m, 6H), 7.36-7.30 (d, J=7.5 Hz, 2H), 3.10 (s, 4H). $^{13}$C NMR (125 MHz, MeOD): δ 159.57, 145.63, 140.43, 135.40, 135.11, 131.52, 130.56, 130.00, 126.82, 124.43, 38.32.

Example 1d

N-(3-(1-hydroxy-2-(3-(thiophene-2-carboximidamido)phenoxy)ethyl)phenyl)thiophene-2-carboximidamide (4)

$^1$H NMR (500 MHz, DMSO-d6): δ 8.28-8.10 (m, 3H), 8.09-7.99 (m, 1H), 7.97-7.92 (m, 1H), 7.59-7.52 (m, 2H), 7.46 (t, J=8.5 Hz, 1H), 7.42-7.34 (m, 3H), 7.33-7.25 (m, 1H), 7.11-6.97 (m, 2H), 5.03 (m, 1H), 4.20-4.01 (m, 1H), 3.80-3.65 (m, 1H). $^{13}$C NMR (126 MHz, DMSO-d6): δ 159.34, 156.89, 156.41, 144.28, 144.20, 140.84, 134.86, 134.62, 134.34, 130.78, 129.63, 129.01, 128.53, 128.30, 126.28, 124.35, 123.35, 117.73, 114.78, 111.81, 72.97, 70.11.

Example 1e

N,N'-((ethane-1,2-diylbis(oxy))bis(3,1-phenylene))bis(thiophene-2-carboximidamide) (5)

$^1$H NMR (500 MHz, MeOD): δ 8.16-8.06 (m, 4H), 7.54 (t, J=8.0 Hz, 2H), 7.40 (t, J=4.5 Hz, 2H), 7.20-7.12 (m, 4H), 7.09 (d, J=8.0 Hz, 2H), 4.46 (s, 4H). $^{13}$C NMR (125 MHz, MeOD): δ 161.61, 159.39, 147.54, 136.67, 135.47, 135.16, 132.49, 129.99, 119.00, 116.52, 113.01, 68.19.

Example 1f

N,N'-((propane-1,3-diylbis(oxy))bis(3,1-phenylene))bis(thiophene-2-carboximidamide) (6)

$^1$H NMR (500 MHz, DMSO-d6): δ 8.19 (d, J=6.0 Hz, 1H), 8.14 (d, J=4.0 Hz, 1H), 7.47 (t, J=8.0 Hz, 1H), 7.39 (t, J=4.0 Hz, 1H), 7.14-7.08 (s, 1H), 7.08-6.98 (m, 1H), 4.20 (t, J=6.0 Hz, 1H), 2.23 (t, J=6.0 Hz, 1H). $^{13}$C NMR (125 MHz, DMSO-d6): δ 159.33, 156.48, 147.90, 135.61, 134.86, 134.53, 130.85, 128.57, 117.72, 114.69, 111.69, 64.41, 28.38.

Example 1g

N-(3-(2-((3-(thiophene-2-carboximidamido)benzyl)amino)ethyl)phenyl)thiophene-2-carboximidamide (7)

$^1$H NMR (500 MHz, MeOD): δ 8.15-8.05 (m, 4H), 7.79 (s, 1H), 7.73-7.69 (m, 2H), 7.63-7.54 (m, 2H), 7.53-7.46 (m, 2H), 7.44-7.36 (m, 3H), 4.40 (s, 2H), 3.46 (t, J=7.5 Hz, 2H), 3.23 (t, J=7.5 Hz, 2H). $^{13}$C NMR (125 MHz, MeOD): δ 159.44, 140.62, 136.25, 135.71, 135.51, 135.40, 135.36, 135.17, 134.97, 132.33, 132.06, 131.83, 130.79, 130.04, 130.01, 128.59, 127.89, 127.42, 125.69, 51.90, 43.75, 33.00.

Example 1h

N-(4-(2-((3-(thiophene-2-carboximidamido)benzyl)amino)ethyl)phenyl)thiophene-2-carboximidamide (8)

$^1$H NMR (500 MHz, MeOD): δ 8.15-8.05 (m, 4H), 7.79 (s, 1H), 7.71 (d, J=5.0 Hz, 2H), 7.58 (d, J=8.0 Hz, 3H), 7.48 (d, J=8.0 Hz, 2H), 7.44-7.37 (m, 2H), 4.40 (s, 2H), 3.47-3.40 (t, J=7.5 Hz, 2H), 3.26-3.19 (t, J=7.5 Hz, 2H). $^{13}$C NMR (125 MHz, MeOD): δ 164.83, 142.46, 139.16, 135.72, 135.49, 135.42, 135.11, 134.96, 132.35, 132.33, 132.05, 131.82, 130.18, 130.05, 130.00, 128.58, 127.92, 127.41, 124.66, 51.87, 43.75, 32.89.

Example 1i

N-(3-((pyrrolidin-3-yloxy)methyl)phenyl)thiophene-2-carboximidamide (9)

$^1$H NMR (500 MHz, MeOD): δ 8.13-8.02 (m, 4H), 7.61 (t, J=7.5 Hz, 2H), 7.57-7.48 (m, 4H), 7.47-7.36 (m, 4H), 4.69 (s, 4H), 3.57-3.51 (m, 1H), 3.47-3.41 (m, 4H), 3.38-3.34 (m, 2H), 2.39-2.27 (m, 2H), 2.21-2.07 (m, 2H). $^{13}$C NMR (125 MHz, MeOD): δ 157.98, 145.72, 142.06, 135.70, 135.50, 135.15, 131.60, 130.01, 129.29, 126.04, 125.79, 78.61, 71.02, 51.79, 45.13, 31.40.

Example 1j

N-(3-(2-(pyrrolidin-3-ylamino)ethyl)phenyl)thiophene-2-carboximidamide (10)

$^1$H NMR (500 MHz, MeOD): δ 8.14-8.06 (m, 2H), 7.61 (t, J=8.0 Hz, 1H), 7.54-7.48 (m, 2H), 7.44-7.37 (m, 2H), 3.80-3.74 (m, 2H), 3.46-3.40 (m, 3H), 3.24-3.19 (m, 2H), 2.68-2.53 (m, 1H), 2.43-2.31 (m, 1H). $^{13}$C NMR (125 MHz, MeOD): δ 159.51, 140.25, 139.01, 135.52, 135.17, 132.17, 130.97, 130.25, 130.01, 127.58, 125.95, 68.15, 57.65, 48.00, 45.89, 33.20, 28.70.

Example 1k

N-(3-((5-(dimethylamino)naphthalene-1-sulfonamido)methyl)phenyl)thiophene-2-carboximidamide (11)

$^1$H NMR (500 MHz, DMSO-d6): δ 8.65 (t, J=6.0 Hz, 1H), 8.53 (d, J=8.5 Hz, 1H), 8.39 (d, J=8.5 Hz, 1H), 8.20 (d, J=4.5 Hz, 1H), 8.18-8.11 (m, 2H), 7.66 (td, J=8.0, 4.5 Hz, 2H), 7.45-7.38 (m, 2H), 7.32-7.24 (m, 3H), 4.11 (d, J=6.0 Hz, 2H), 2.88 (s, 6H). $^{13}$C NMR (125 MHz, DMSO-d6): δ 156.33, 152.08, 145.14, 143.72, 140.09, 136.00, 134.90, 134.54, 134.33, 129.73, 129.28, 128.91, 128.60, 128.37, 127.90, 127.08, 124.16, 124.10, 123.87, 123.83, 45.41, 45.19.

Example 1l

N-(4-(2-(5-(dimethylamino)naphthalene-1-sulfona-mido)ethyl)phenyl)thiophene-2-carboximidamide (12)

$^1$H NMR (500 MHz, DMSO-d6): δ 8.55 (d, J=8.5 Hz, 1H), 8.37 (d, J=8.5 Hz, 1H), 8.18 (d, J=5.0 Hz, 1H), 8.16-8.11 (m, 3H), 7.73-7.58 (m, 2H), 7.46-7.35 (m, 2H), 7.34-7.25 (m, 3H), 3.11-2.99 (m, 2H), 2.91 (s, 6H), 2.75-2.70 (m, 2H). $^{13}$C NMR (125 MHz, DMSO-d6): δ 156.45, 149.27, 141.62, 138.91, 135.92, 134.79, 134.42, 132.64, 130.09, 129.16, 129.06, 128.97, 128.57, 128.36, 127.82, 125.44, 45.24, 34.88.

Example 1m

N-(3-((ethyl(3-fluorophenethyl)amino)methyl)phenyl)thiophene-2-carboximidamide (64)

$^1$H NMR (400 MHz, CD$_3$OD): δ 7.85-7.72 (m, 2H), 7.43 (t, J=7.5 Hz, 1H), 7.31-7.17 (m, 4H), 7.12 (dt, J=7.5, 1.0 Hz, 1H), 7.02 (dt, J=7.5, 1.0 Hz, 1H), 6.97 (dt, J=9.0, 2.5 Hz, 1H), 6.88 (td, J=9.0, 2.5 Hz, 1H), 3.96 (s, 2H), 2.99-2.82 (m, 6H), 1.18 (t, J=7.0 Hz, 3H). $^{13}$C NMR (100 MHz, CD$_3$OD): δ 164.05, 161.62, 141.73 (d, J=7.5 Hz), 135.05, 130.92, 130.00, 129.91, 129.82, 129.80, 127.70, 126.86, 124.80, 124.44, 124.41, 123.27, 115.19 (d, J=20 Hz), 112.72 (d, J=20 Hz), 109.99, 56.82, 53.51, 47.10, 31.10, 9.67.

Example 1n

N-(3-(((3-fluorophenethyl)amino)methyl)phenyl)thiophene-2-carboximidamide (65)

$^1$H NMR (400 MHz, CD$_3$OD): δ 8.18-8.04 (m, 2H), 7.81-7.69 (m, 2H), 7.65 (t, J=7.5 Hz, 1H), 7.58-7.50 (m, 1H), 7.41-7.28 (m, 2H), 7.18-7.06 (m, 2H), 7.03-6.93 (m, 1H), 4.37 (s, 2H), 3.42-3.31 (m, 2H), 3.20-3.10 (m, 2H). $^{13}$C NMR (100 MHz, CD$_3$OD): δ 164.17, 161.74 (s), 139.31 (d, J=7.5 Hz), 134.72, 134.45, 134.22, 133.50, 130.87, 130.55, 130.34 (d, J=7.5 Hz), 128.66, 127.22, 126.47, 124.49, 124.46, 115.30 (d, J=20 Hz), 113.56 (d, J=20 Hz), 109.99, 50.38, 48.27, 31.49 (d, J=2.0 Hz).

The compounds of FIG. 3, (Schemes 10-15) were characterized, as provided below in Examples 2-11.

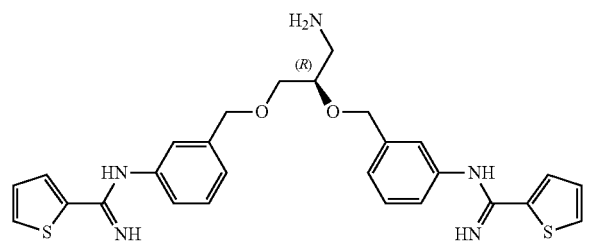

(R)-QJ-II-183

$^1$H NMR (500 MHz, CDCl$_3$) δ 7.35-7.32 (m, 4H), 7.25-7.19 (m, 2H), 6.99-6.94 (m, 4H), 6.90 (s, 2H), 6.83 (d, J=7.5 Hz, 2H), 4.88 (br, 4H), 4.60 (d, J=5.0 Hz, 1H), 4.50 (d, J=5.0 Hz, 1H), 4.44 (s, 2H), 3.52-3.48 (m, 3H), 2.80-2.70 (m, 2H); $^{13}$C NMR (126 MHz, DMSO) δ $^{13}$C NMR (126 MHz, CDCl$_3$) δ 149.88, 149.09, 140.51, 139.90, 139.51, 129.55, 128.96, 127.30, 126.05, 122.76, 122.64, 121.33, 121.30, 121.15, 79.28, 73.36, 72.03, 70.54, 50.73, 43.26 ppm; MS (ESI): 520.8 (M+H)$^+$.

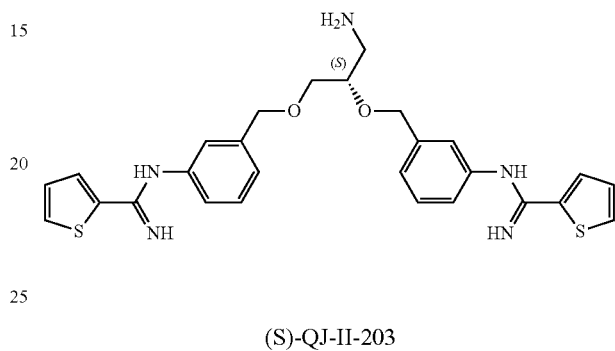

(S)-QJ-II-203

$^1$H NMR (500 MHz, CDCl$_3$) δ 7.36-7.32 (m, 4H), 7.25-7.19 (m, 2H), 6.99-6.94 (m, 4H), 6.90 (s, 2H), 6.82 (d, J=7.5 Hz, 2H), 4.88 (br, 4H), 4.60 (d, J=5.0 Hz, 1H), 4.50 (d, J=5.0 Hz, 1H), 4.44 (s, 2H), 3.52-3.48 (m, 3H), 2.80-2.70 (m, 2H); $^{13}$C NMR (126 MHz, DMSO) δ $^{13}$C NMR (126 MHz, CDCl$_3$) δ 149.88, 149.10, 140.51, 139.90, 139.51, 129.55, 128.96, 127.30, 126.05, 122.76, 122.64, 121.33, 121.30, 121.16, 79.28, 73.36, 72.03, 70.54, 50.72, 43.26 ppm; MS (ESI): 520.6 (M+H)$^+$.

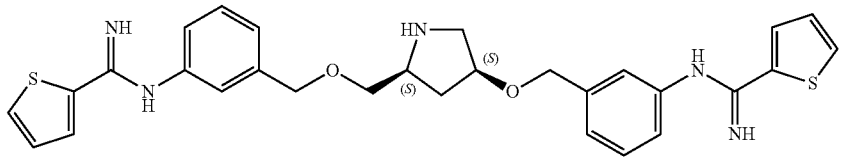

(S,S)-QJ-II-195

$^1$H NMR (500 MHz, CDCl$_3$) δ 7.42 (t, J=5.0 Hz, 2H), 7.40 (d, J=4.0 Hz, 1H), 7.36 (d, J=4.0 Hz, 1H), 7.30 (t, J=7.5 Hz, 2H), 7.08-7.00 (m, 4H), 6.95 (d, J=7.5 Hz, 2H), 6.91 (d, J=7.5 Hz, 2H), 4.90 (br, 2H), 4.53 (s, 2H), 4.44 (d, J=5.0 Hz, 2H), 4.13-4.11 (m, 1H), 3.56-3.53 (m, 2H), 3.30-3.27 (m, 1H), 3.10 (d, J=5.0 Hz, 1H), 2.88 (dd, J=5.0 Hz, J=10.0 Hz, 1H), 2.13-2.09 (m, 1H), 1.81 (br, 2H), 1.65-1.60 (m, 1H); δ $^{13}$C NMR (126 MHz, CDCl$_3$) δ 149.83, 149.75, 149.02, 140.56, 140.50, 139.82, 139.69, 129.53, 128.98, 128.93, 127.28, 125.97, 122.70, 122.54, 121.21, 121.09, 79.90, 73.18, 72.88, 70.90, 57.86, 52.58, 50.85, 35.19 ppm; MS (ESI): 546.3 (M+H)$^+$.

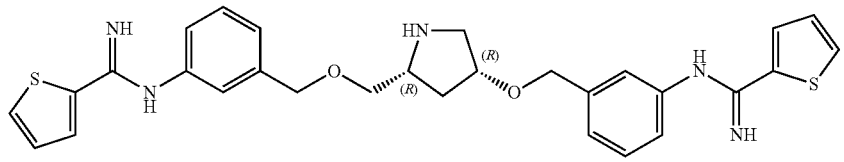

(R,R)-QJ-II-187

¹H NMR (500 MHz, CDCl₃) δ 7.42 (t, J=5.0 Hz, 2H), 7.40 (d, J=4.0 Hz, 1H), 7.36 (d, J=4.0 Hz, 1H), 7.30 (t, J=7.5 Hz, 2H), 7.08-7.00 (m, 4H), 6.95 (d, J=7.5 Hz, 2H), 6.91 (d, J=7.5 Hz, 2H), 4.90 (br, 2H), 4.53 (s, 2H), 4.44 (d, J=5.0 Hz, 2H), 4.13-4.11 (m, 1H), 3.56-3.53 (m, 2H), 3.30-3.27 (m, 1H), 3.10 (d, J=5.0 Hz, 1H), 2.88 (dd, J=5.0 Hz, J=10.0 Hz, 1H), 2.13-2.09 (m, 1H), 1.81 (br, 2H), 1.65-1.60 (m, 1H); δ ¹³C NMR (126 MHz, CDCl₃) δ 149.83, 149.75, 149.02, 140.56, 140.50, 139.82, 139.69, 129.53, 128.98, 128.93, 127.28, 125.97, 122.70, 122.54, 121.21, 121.09, 79.90, 73.18, 72.88, 70.90, 57.86, 52.58, 50.85, 35.19 ppm; MS (ESI): 546.2 (M+H)⁺.

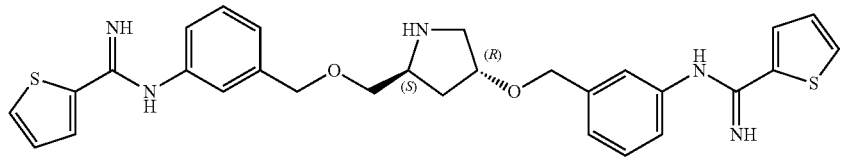

(S,R)-QJ-II-194

¹H NMR (500 MHz, CDCl₃) δ 7.43 (d, J=5.0 Hz, 2H), 7.40 (d, J=4.5 Hz, 2H), 7.32 (t, J=7.5 Hz, 2H), 7.07 (t, J=4.5 Hz, 2H), 7.03 (d, J=7.5 Hz, 2H), 6.97 (s, 2H), 6.91 (d, J=7.5 Hz, 2H), 4.87 (br, 2H), 4.51 (d, J=5.0 Hz, 2H), 4.47 (d, J=5.0 Hz, 2H), 4.13-4.11 (m, 1H), 3.55-3.53 (m, 1H), 3.47-3.45 (m, 1H), 3.42-3.38 (m, 1H), 3.09-2.95 (m, 1H), 2.00 (dd, J=7.5 Hz, J=13.5 Hz, 1H), 1.84 (br, 2H), 1.65-1.59 (m, 1H); δ ¹³C NMR (126 MHz, CDCl₃) δ 149.75, 148.97, 140.51, 139.85, 139.75, 129.56, 129.51, 128.99, 127.29, 125.97, 122.65, 122.54, 121.14, 121.11, 121.04, 79.95, 73.39, 73.20, 70.85, 56.73, 52.47, 50.85, 35.15; MS (ESI): 546.2 (M+H)⁺.

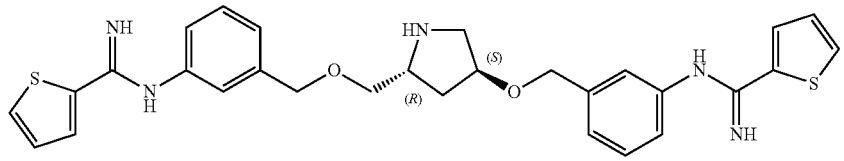

(R,S)-QJ-II-199

¹H NMR (500 MHz, CDCl₃) δ 7.43 (d, J=5.0 Hz, 2H), 7.40 (d, J=4.5 Hz, 2H), 7.32 (t, J=7.5 Hz, 2H), 7.07 (t, J=4.5 Hz, 2H), 7.02 (d, J=7.5 Hz, 2H), 6.97 (s, 2H), 6.91 (d, J=7.5 Hz, 2H), 4.87 (br, 2H), 4.51 (d, J=5.0 Hz, 2H), 4.47 (d, J=5.0 Hz, 2H), 4.13-4.10 (m, 1H), 3.55-3.53 (m, 1H), 3.47-3.45 (m, 1H), 3.42-3.38 (m, 1H), 3.09-2.95 (m, 1H), 2.00 (dd, J=7.5 Hz, J=13.5 Hz, 1H), 1.84 (br, 2H), 1.65-1.59 (m, 1H); δ ¹³C NMR (126 MHz, CDCl₃) δ 149.75, 148.97, 140.51, 139.86, 139.75, 129.56, 129.52, 128.99, 127.29, 125.97, 122.65, 122.54, 121.14, 121.11, 121.03, 79.95, 73.39, 73.20, 70.86, 56.73, 52.47, 50.85, 35.15; MS (ESI): 546.3 (M+H)⁺.

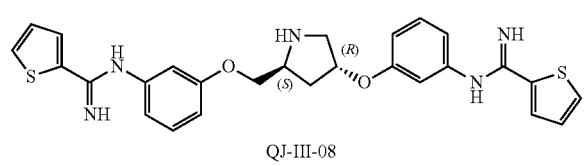

QJ-III-08

QJ-III-08: ¹H NMR (500 MHz, CD₃OD) δ 7.64 (s, 1H), 7.56 (d, J=10.0 Hz, 1H), 7.29 (t, J=8.0 Hz, 2H), 7.13 (t, J=12.0 Hz, 1H), 7.00 (t, J=8.0 Hz, 3H), 6.70 (dd, J=17.5 Hz, J=8.0 Hz, 1H), 6.61-6.55 (m, 3H), 6.35-6.30 (m, 2H), 4.03-3.92 (m, 2H), 3.77-3.70 (m, 1H), 3.37 (s, 2H), 3.15-3.08 (m, 1H), 2.25-2.19 (m, 1H), 1.99-1.92 (m, 1H); ¹³C NMR (126 MHz, CD₃OD) δ 161.44+161.32, 160.04, 159.87, 153.92, 151.38, 150.14+150.06, 140.96, 131.43+131.37, 130.92+130.87, 129.94+129.91, 128.53, 128.41, 116.20+116.10, 111.91, 110.92+110.83, 109.86, 109.71+109.65, 106.44, 105.43, 104.02, 103.01, 79.18+78.92, 71.28+71.04, 57.87+57.82, 53.26, 36.68+36.66 ppm. MS (ESI): 518.3 (M+H)⁺.

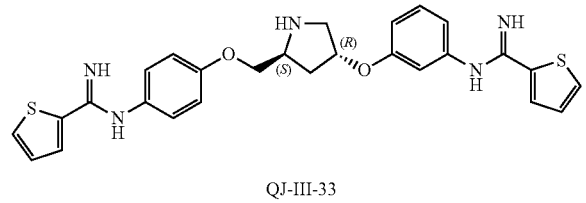

QJ-III-33

III-33: ¹H NMR (500 MHz, CD₃OD) δ 7.53-7.50 (m, 2H), 7.46-7.44 (m, 2H), 7.03-7.00 (m, 2H), 6.91-6.87 (m, 3H), 6.82-6.80 (m, 2H), 6.59-6.48 (m, 1H), 6.45 (s, 1H), 6.24-6.21 (m, 1H), 4.26-4.12 (m, 1H), 3.93-3.85 (m, 2H), 3.66-3.62 (s, 1H), 3.01 (dd, J=18.5 Hz, J=12.5 Hz, 1H), 2.31-2.26 (m, 1H), 2.15-2.07 (m, 1H), 1.90-1.81 (m, 1H); ¹³C NMR (126 MHz, CD₃OD) δ 164.04, 162.56, 162.38, 159.27, 133.99, 133.47, 132.49, 132.32, 130.96, 130.92, 127.13, 119.19, 118.65, 114.46, 113.36, 112.24, 109.02, 106.60, 81.74+81.46, 74.17, 60.39, 55.87+55.80, 39.18 ppm. MS (ESI): 518.2 (M+H)⁺.

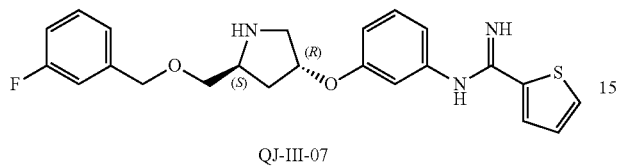

QJ-III-07

QJ-III-07: ¹H NMR (500 MHz, CDCl₃) δ 7.45 (dd, J=9.0 Hz, J=5.0 Hz, 2H), 7.25-7.22 (m, 1H), 7.15 (d, J=8.0 Hz, 1H), 7.03-6.97 (m, 3H), 6.89 (t, J=8.0 Hz, 1H), 6.50 (dd, J=4.0 Hz, J=2.0 Hz, 2H), 6.43 (s, 1H), 4.80 (br, 2H), 4.76 (t, J=6.0 Hz, 1H), 4.49-4.43 (m, 2H), 3.57-3.54 (m, 1H), 3.44-3.35 (m, 2H), 3.18 (dd, J=12.0 Hz, J=4.0 Hz, 1H), 3.07 (d, J=12.0 Hz, 1H), 2.03 (dd, J=14.0 Hz, J=7.0 Hz, 1H), 1.76-1.70 (m, 1H); ¹³C NMR (126 MHz, CDCl₃) δ 163.90, 161.95, 158.67, 150.27, 149.65, 141.01+140.96, 140.45, 130.32, 129.93+129.87, 129.04, 127.32, 125.99, 122.94, 114.52+114.41+114.35+114.24, 114.08, 110.87, 108.69, 78.18, 73.42, 72.52, 56.94, 52.85, 35.66 ppm; MS (ESI): 426.3 (M+H)⁺.

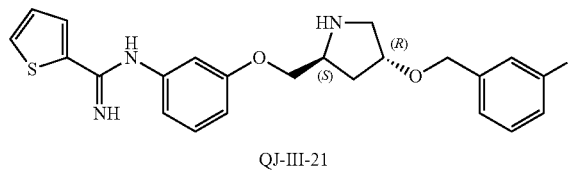

QJ-III-21

QJ-III-21: ¹H NMR (500 MHz, CDCl₃) δ 7.37 (d, J=5.0 Hz, 1H), 7.33 (d, J=3.5 Hz, 1H), 7.26 (q, J=9.5 Hz, J=7.5 Hz, 1H), 7.16 (t, J=8.0 Hz, 1H), 7.03-6.98 (m, 3H), 6.90 (t, J=8.0 Hz, 1H), 6.56-6.48 (m, 2H), 6.25-6.17 (m, 1H), 4.77 (br, 2H), 4.43-4.39 (m, 2H), 4.09 (s, 1H), 3.87-3.79 (m, 2H), 3.70-3.56 (m, 1H), 3.07-3.04 (m, 2H), 2.05 (dd, J=13.5 Hz, J=7.0 Hz, 1H), 1.69-1.64 (m, 1H); ¹³C NMR (126 MHz, CDCl₃) δ 163.93, 161.97, 160.06, 150.21+149.60, 147.71, 141.09+141.03, 140.49, 130.23, 129.96+129.90+129.02, 127.30, 125.92, 122.86, 114.53+114.38+114.36+114.20, 109.89+108.04, 107.85, 104.59, 101.70, 80.18, 71.01, 70.11, 56.20, 52.51, 35.13 ppm; MS (ESI): 426.6 (M+H)⁺.

Example 12

NOS inhibition assays were undertaken for compounds I-12 and 64-65 of FIG. 1 and for the compounds of FIG. 3, and the results are provided in Tables 1 and 2, respectively.

TABLE 1

Inhibition of NOS isozymes by synthetic inhibitors.[a]

| | Ki (μM) | | | Selectivity[b] | |
|---|---|---|---|---|---|
| No. | nNOS | iNOS | eNOS | n/i | n/e |
| 1 | 0.787 | 66.4 | 177.3 | 84 | 225 |
| 2 | 6.470 | 19.4 | 491.7 | 3 | 76 |
| 3 | 0.739 | 103.8 | 66.0 | 141 | 89 |
| 4 | 0.819 | 10.1 | 5.2 | 12 | 6 |
| 5 | 0.130 | 66.8 | 13.7 | 513 | 105 |
| 6 | 0.237 | 12.6 | 4.0 | 53 | 17 |
| 7 | 0.005 | 1.3 | 2.2 | 235 | 407 |
| 8 | 0.005 | 1.7 | 2.7 | 312 | 495 |
| 9 | 0.139 | 36.5 | 15.8 | 263 | 113 |
| 10 | 0.131 | 6.9 | 40.8 | 53 | 311 |
| 11 | 0.498 | 34.3 | 115.4 | 69 | 232 |
| 12 | 0.243 | 142.4 | 7.28 | 586 | 30 |
| 64 | 0.073 | 12.1 | 21.7 | 166 | 297 |
| 65 | 0.011 | 1.6 | 0.9 | 145 | 82 |

[a]The compounds were evaluated for in vitro inhibition against three NOS isozymes: rat nNOS, bovine eNOS and marine iNOS using known literature methods. (Hevel, J.M.; Marletta, M.A. Nitric-oxide synthase assays. Method Enzymol. 1994, 233, 250-258).
[b]Each of n/e and n/i is the inverse of the ratio of K$_i$ (eNOS or iNOS) to K$_i$ (nNOS).

TABLE 2

Inhibition of NOS isozymes by synthetic inhibitors.[a]

| | Ki [μM] | | | Selectivity[b] | |
|---|---|---|---|---|---|
| Compounds | nNOS | eNOS | iNOS | n/e | n/i |
| QJ-II-183 | 0.0590 | 12.44 | 8.11 | 210 | 137 |
| QJ-II-203 | 0.0147 | 16.68 | 4.73 | 1134 | 322 |
| QJ-II-187 | 0.0281 | 3.63 | 1.99 | 130 | 71 |
| QJ-II-194 | 0.0132 | 2.47 | 1.11 | 190 | 85 |
| QJ-II-195 | 0.0221 | 1.45 | 2.11 | 658 | 96 |
| QJ-II-199 | 0.0214 | 3.17 | 1.23 | 151 | 58 |
| QJ-III-07 | 0.0684 | 5.89 | 6.17 | 86 | 90 |
| QJ-III-08 | 0.0282 | 3.34 | 2.42 | 119 | 86 |
| QJ-III-21 | 0.101 | 1.86 | 9.28 | 18 | 92 |
| QJ-III-33 | 0.0270 | 1.15 | 4.40 | 142 | 163 |

[a] K$_m$ values of rat nNOS, 1.3 μM; murine iNOS, 8.2 μM; bovine eNOS, 1.7 μM). K$_i$ = IC$_{50}$/(1 + [S]/K$_M$).
[b] Each of n/e and n/i is the inverse of the ratio of K$_i$ (eNOS or iNOS) to K$_i$ (nNOS).

We claim:

1. A compound of a formula

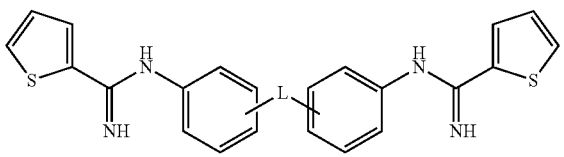

wherein L is a divalent CH₂CH₂ moiety with a meta-relationship to each said thiophene-2-carboximidamide moiety of said compound; or a salt thereof.

* * * * *

UNITED STATES PATENT AND TRADEMARK OFFICE
CERTIFICATE OF CORRECTION

| | | |
|---|---|---|
| PATENT NO. | : 8,735,606 B2 | Page 1 of 1 |
| APPLICATION NO. | : 14/015551 | |
| DATED | : May 27, 2014 | |
| INVENTOR(S) | : Richard B. Silverman et al. | |

It is certified that error appears in the above-identified patent and that said Letters Patent is hereby corrected as shown below:

On the title page item (54) and in the Specification Column 1, lines 1-3
"THIOPHENE-2-CARBOXIMIDAMIDE BASED SELECTIVE NEURONAL NITRIC OXIDE INHIBITORS" should read --THIOPHENE-2-CARBOXIMIDAMIDE BASED SELECTIVE NEURONAL NITRIC OXIDE SYNTHASE INHIBITORS--

Signed and Sealed this
Twenty-second Day of March, 2016

Michelle K. Lee
*Director of the United States Patent and Trademark Office*